(12) United States Patent
Soden et al.

(10) Patent No.: US 10,071,244 B2
(45) Date of Patent: Sep. 11, 2018

(54) THORACOSCOPIC ELECTROPORATION DEVICE WITH A SUCTION HEAD AND WITH NEEDLE ELECTRODES

(71) Applicant: UNIVERSITY COLLEGE CORK—NATIONAL UNIVERSITY OF IRELAND, CORK, Cork (IE)

(72) Inventors: Declan Soden, Cork (IE); John Hinchion, Cork (IE)

(73) Assignee: University College Cork—National University of Ireland, Cork, Cork (IE)

( * ) Notice: Subject to any disclaimer, the term of this patent is extended or adjusted under 35 U.S.C. 154(b) by 135 days.

(21) Appl. No.: 14/652,740

(22) PCT Filed: Dec. 19, 2013

(86) PCT No.: PCT/EP2013/077521
§ 371 (c)(1),
(2) Date: Jun. 16, 2015

(87) PCT Pub. No.: WO2014/096275
PCT Pub. Date: Jun. 26, 2014

(65) Prior Publication Data
US 2015/0328449 A1 Nov. 19, 2015

(30) Foreign Application Priority Data

Dec. 21, 2012 (IE) .................................. 2012/0551

(51) Int. Cl.
*A61N 1/32* (2006.01)
*A61N 1/05* (2006.01)
(Continued)

(52) U.S. Cl.
CPC ........ *A61N 1/325* (2013.01); *A61B 17/00234* (2013.01); *A61B 18/1482* (2013.01);
(Continued)

(58) Field of Classification Search
CPC ...... A61N 1/325; A61N 1/0502; A61N 1/327; A61B 17/00234; A61B 2017/308; A61B 2018/1475; A61B 2018/00291
See application file for complete search history.

(56) References Cited

U.S. PATENT DOCUMENTS 5,951,547 A * 9/1999 Gough ............... A61B 18/1477
606/41
2006/0241733 A1 10/2006 Zhang et al.
(Continued)

OTHER PUBLICATIONS

International Search Report; PCT/EP2013/077521; dated Mar. 7, 2014.
(Continued)

*Primary Examiner* — Bradley J Osinski
(74) *Attorney, Agent, or Firm* — Studebaker & Brackett PC

(57) ABSTRACT

A thoracoscopic electroporation device for carrying out electroporation on tissue includes a suction head and a plurality of needle electrodes. The needle electrodes include a central needle providing a first electrode and a plurality of second needles which are spaced-apart around the periphery of the suction head. The electrodes are movable from a retracted configuration to a deployed configuration and in the deployed configuration the needles extend from the suction head. The suction head has a retracted delivery configuration and an expanded deployed configuration. The suction head includes a suitable flexible material for biasing the suction head into the expanded deployed configuration. The suction head has channels for the needles and the needles are movable through the channels from the retracted to the deployed configuration. In the deployed configuration, the central first needle extends beyond the peripheral needles.

15 Claims, 36 Drawing Sheets

(51) Int. Cl.
*A61B 17/00* (2006.01)
*A61B 18/14* (2006.01)
*A61B 17/30* (2006.01)
*A61B 18/00* (2006.01)

(52) U.S. Cl.
CPC ........... *A61N 1/0502* (2013.01); *A61N 1/327* (2013.01); *A61B 2017/00292* (2013.01); *A61B 2017/00809* (2013.01); *A61B 2017/00867* (2013.01); *A61B 2017/308* (2013.01); *A61B 2018/00291* (2013.01); *A61B 2018/00541* (2013.01); *A61B 2018/00613* (2013.01); *A61B 2018/143* (2013.01); *A61B 2018/1475* (2013.01)

(56) References Cited

U.S. PATENT DOCUMENTS

2007/0287999 A1    12/2007  Malecki et al.
2008/0009747 A1*   1/2008   Saadat ................. A61B 1/0008
                                                                600/471
2012/0226271 A1    9/2012   Callas et al.

OTHER PUBLICATIONS

Written Opinion of the International Searching Authority; PCT/EP2013/077521; dated Mar. 7, 2014.

* cited by examiner

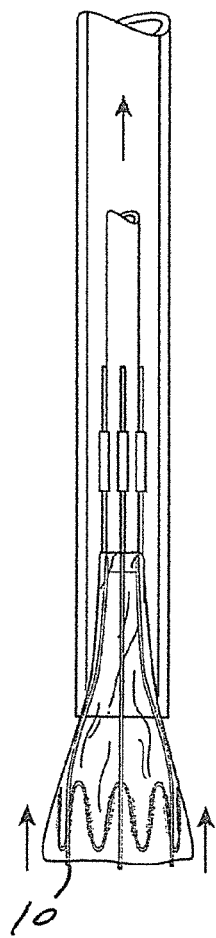
Fig. 6
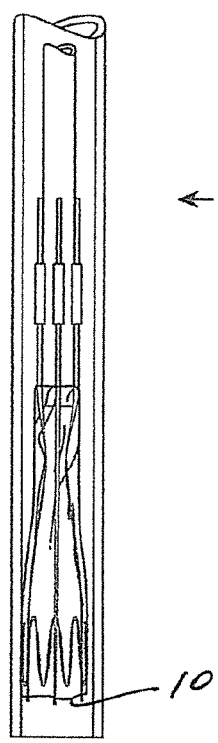
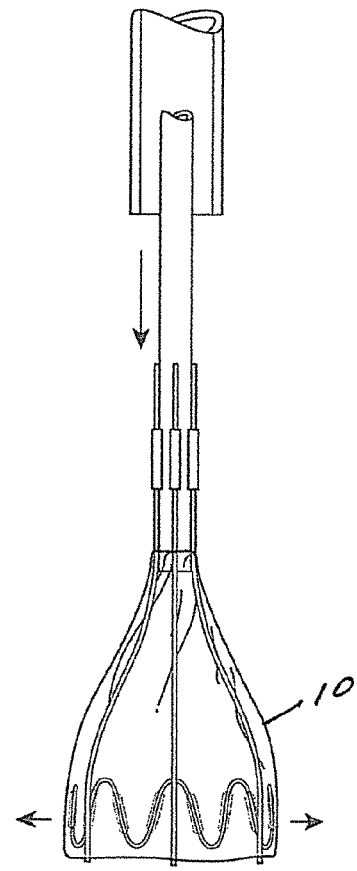
Fig. 5
Fig. 4

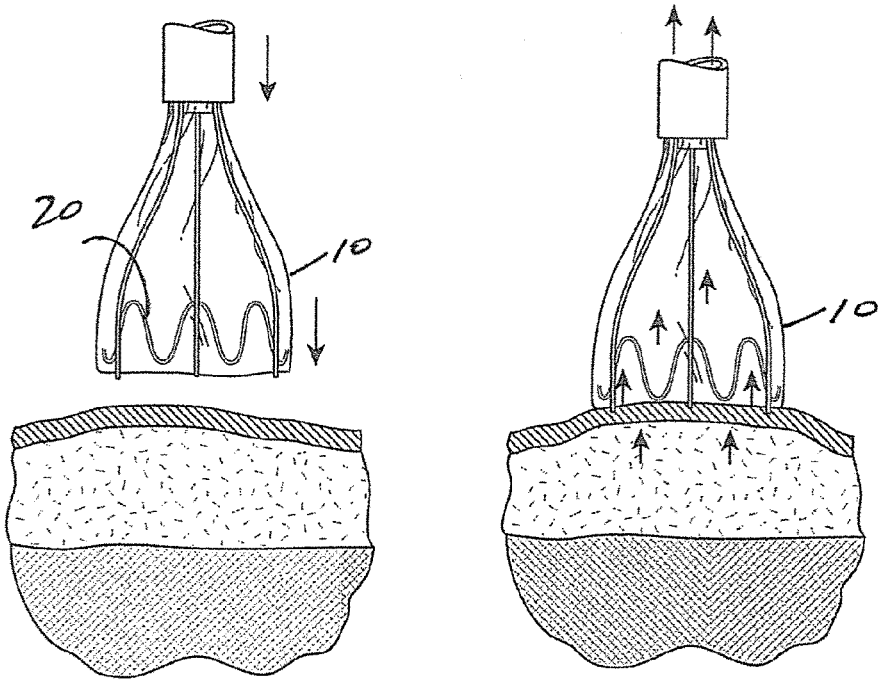
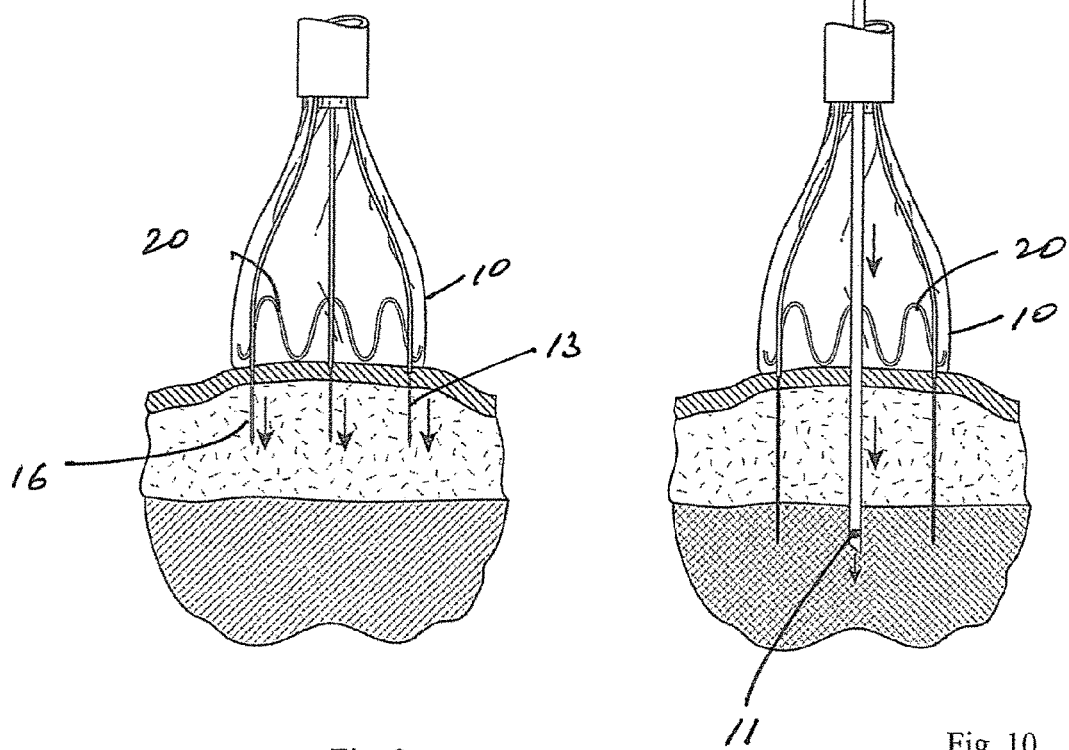
Fig. 7　　Fig. 8
Fig. 9　　Fig. 10

The correlation between tumor growth and tumor interstitial pressure.

Lewis Lung Carcinoma cell line LLC

THORACOSCOPIC ELECTROPORATION DEVICE WITH A SUCTION HEAD AND WITH NEEDLE ELECTRODES

INTRODUCTION

This invention relates to devices and apparatus for use in carrying out a prophylactic or treatment procedure on tissue. The invention also relates to a method of prophylaxis or treatment of tissue utilising a device or apparatus of the invention.

Lung cancer is not adequately addressed by existing therapies. Currently between 80%-85% of patients are deemed unsuitable for surgical treatment. Radiotherapy or Radio frequency ablation (RFA), for example using a Leveen needle, has the disadvantage eliciting a therapeutic effect by using heat to denature and immediately destroy all surrounding tissues.

STATEMENTS OF INVENTION

According to the invention there is provided a thoracoscopic electroporation device for carrying out electroporation on tissue comprising a suction head and a plurality of needle electrodes which are adapted for carrying out electroporation on tissue, the suction head having a retracted delivery configuration and an expanded deployed configuration and biasing means for biasing the suction head into the expanded deployed configuration.

In one embodiment the biasing means comprises a biasing element.

The biasing means may comprise at least two biasing elements which are axially spaced-apart with respect to a longitudinal axis of the device.

In one case the biasing element comprises a shape memory material.

The biasing element may comprise an expansile material.

In one embodiment the biasing element comprises a balloon which is expandable from a retracted delivery configuration to an expanded deployed configuration.

In one case the suction head is cup-shaped.

The suction head in one embodiment comprises an inner part and an outer part which extends radially outwardly of the inner part in the deployed configuration. The outer part may be flexible with respect to the inner part. In one case the inner part is of a rigid material and the outer part is of a flexible material. The outer part may be movable from a retracted delivery configuration to an extended deployed configuration.

In one embodiment the suction head comprises passages for at least some of the needles, the needles being movable though the passageways from the retracted configuration to the deployed configuration.

The needle electrodes may comprise at least one needle providing a first electrode and a plurality of second needles providing a second electrode. At least some of the electrodes may be movable from a retracted configuration to a deployed configuration, the needles extending from the suction head in the deployed configuration.

In one embodiment the second needles are spaced-apart around the periphery of the suction head.

At least some of the second electrodes are movable from a retracted configuration to a deployed configuration, the second needles extending from the suction head in the deployed configuration The first needle may be located generally along a central longitudinal axis of the suction head in the retracted configuration.

The first needle may be located generally along a central longitudinal axis of the suction head in the deployed configuration.

In one embodiment, in the deployed configuration the first electrode needle extends beyond the second electrode needles.

In one embodiment the plurality of second needles extend generally longitudinally along the suction head in both the retracted and deployed configurations.

In one embodiment the device comprises a shaft which extends from the suction head.

The shaft may be rigid over at least part of its length. Alternatively or additionally the shaft is flexible over at least part of its length. Alternatively or additionally the shaft is malleable over at least part of its length.

The device may comprise a vacuum applying means for gripping the suction head to tissue.

In one embodiment the first needle electrode is a hollow needle. Vacuum may be applied using the hollow first needle electrode. A therapeutic agent may be applied using the first needle electrode.

Also provided is a method for carrying out electroporation on tissue comprising:—
providing a suction head and a plurality of needle electrodes, the suction head having a retracted delivery configuration and an expanded deployed configuration and biasing means for biasing the suction head into the expanded deployed configuration;
delivering the suction head to tissue in the retracted configuration;
deploying the suction head at a site of interest;
applying a vacuum to the suction head;
advancing the needles from the deployed suction head; and
using the needle electrodes, applying electroporation to tissue at the site of interest.

In one embodiment the method comprises the step of delivering a therapeutic agent to the tissue at the site of interest before, during, or after applying electroporation. The therapeutic agent may be delivered through at least one of the needles.

In one case the site of interest is in the region of a lung.

According to the invention there is provided apparatus for use in carrying out electroporation on tissue, especially a thoracoscopic electroporation device comprising a suction head and a plurality of needle electrodes.

In one embodiment the needle electrodes comprise at least one needle providing a first electrode and a plurality of second needles providing a second electrode.

At least some of the electrodes may be movable from a retracted configuration to a deployed configuration, the needles extending from the suction head in the deployed configuration.

In one case the second needles are spaced-apart around the periphery of the suction head.

The first needle may be located generally along a central longitudinal axis of the suction head.

In one embodiment the suction head has a retracted delivery configuration and an expanded deployed configuration. The suction head may comprise a flexible material. The suction head may comprise biasing means for biasing the suction head into the expanded deployed configuration. The biasing means may comprise a biasing element of a shape memory material such as Nitinol.

In one embodiment the suction head comprises channels for the needles, the needles being movable through the channels from the retracted to the deployed configuration.

In one case, in the deployed configuration the first electrode needle extends beyond the second electrode needles.

The apparatus may comprise a vacuum applying means for gripping the cup to tissue.

In one embodiment the first needle electrode is a hollow needle. Vacuum may be applied using the hollow first needle electrode. A therapeutic agent may applied be using the first needle electrode.

BRIEF DESCRIPTION OF THE DRAWINGS

The invention will be more clearly understood from the following description of an embodiment thereof, given by way of example only, with reference to the accompanying drawings, in which:

FIGS. 4 to 6 are views illustrating the delivery and deployment of the apparatus;

FIGS. 7 to 10 are views of the apparatus at various stages during use;

DETAILED DESCRIPTION

Figure 1:
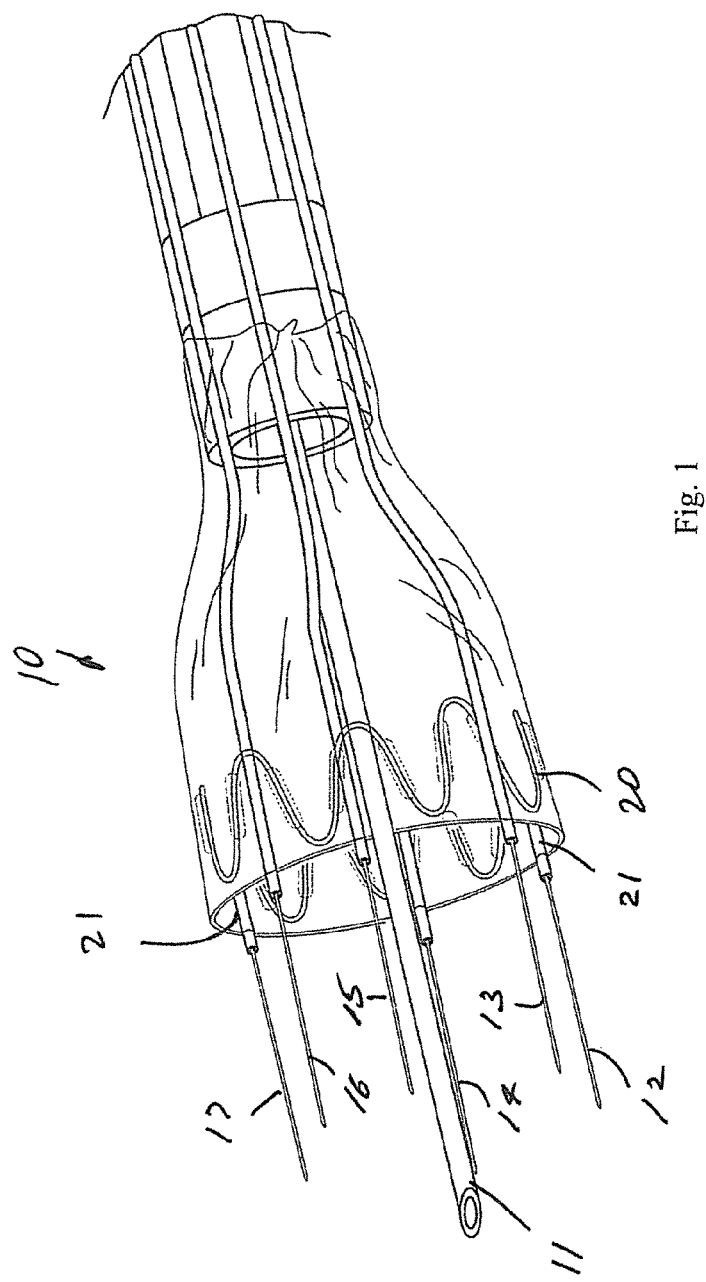
FIG. 1 is a perspective view of an apparatus for carrying out electroporation according to the invention.

Referring to the drawings and initially to FIGS. 1 to 10 thereof there is illustrated an apparatus for use in carrying out electroporation on tissue. The apparatus comprises a suction head 10 and a plurality of needle electrodes. The needle electrodes comprise a central needle 11 providing a first electrode and a plurality of second needles. In this case there are six second needles 12, 13, 14, 15, 16, 17 which are spaced-apart around the periphery of the suction head 1.

The electrodes 12, 13, 14, 15, 16, 17 are movable from a retracted configuration to a deployed configuration and in the deployed configuration illustrated in FIGS. 1, 9 and 10, the needles extend from the suction head 1.

The suction head 1 has a retracted delivery configuration as illustrated in FIG. 4 and an expanded deployed configuration. The suction head 1 comprises a suitable flexible material and biasing means for biasing the suction head into the expanded deployed configuration. The biasing means may, for example, comprise a biasing element 20 (FIG. 3) of a suitable shape memory material such as Nitinol.

The suction head 10 has channels 21 for the needles and the needles are movable through the channels 21 from the retracted to the deployed configuration.

In the deployed configuration, the central first needle 11 may extend beyond the peripheral needles 12, 13, 14, 15, 16, 17.

In this case the central needle 11 providing the first electrode is hollow. This allows a vacuum to be drawn using the central electrode. Alternatively or additionally the central needle 11 may be used to deliver a therapeutic agent such as a chemotherapeutic agent to a tumour in a highly targeted manner.

The second needles which extend around the periphery of the head are more flexible than the central needle. For example, the second needles may be thinner in cross section. This facilitates ease of movement between the retracted configuration during delivery, the expanded configuration on deployment and the retracted configuration on disengagement. In some cases the needles are movable from a radially retracted configuration to a radially expanded configuration. The movement between the radially retracted and expanded configuration may be in direct response to the action of the biasing means. Alternatively or additionally this movement may be as a result of an indirect response to the action of the biasing means. For example, the needles may be extended through sleeves/passages carried by the suction head and/or acted on by the biasing means. In response to the biasing means the sleeves/passageways may expand radially outwardly either with the needles or the sleeves/passageways expanded first and the needles then advanced through the radially expanded sleeves/passageways.

A vacuum may be applied to the suction cup in any suitable manner. In one case a vacuum is applied by drawing air out through the central needle 11.

A therapeutic agent such as a drug or antibody may be applied to the tissue before, during, or after electroporation. The hollow needles provide a convenient delivery system that may be used for localised delivery of the therapeutic agent.

Figure 2:
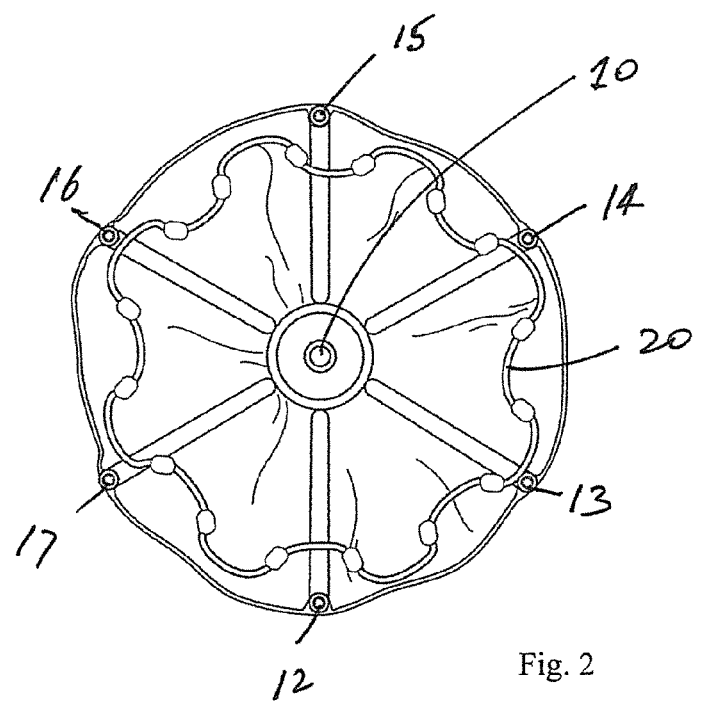
FIG. 2 is an end view of the device of FIG. 1.
Figure 3:
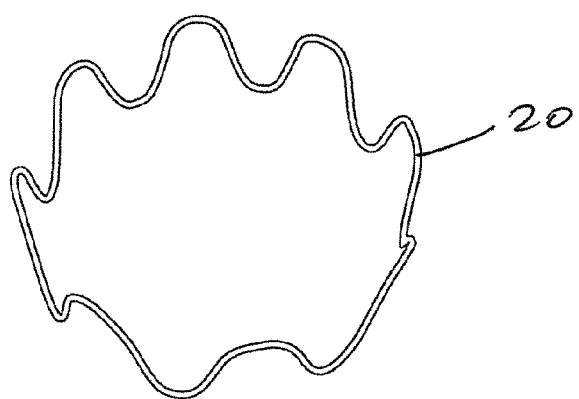
FIG. 3 is a perspective view of a biasing element used in the apparatus.
Figure 11:
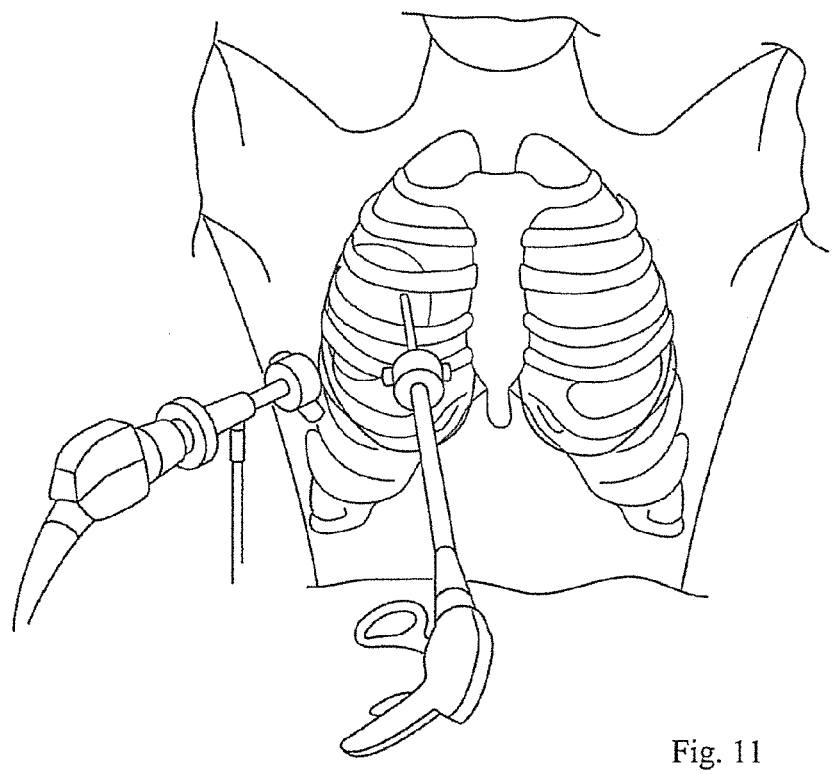
FIGS. 11 to 12 illustrate steps in one use of the apparatus.
Figure 12:
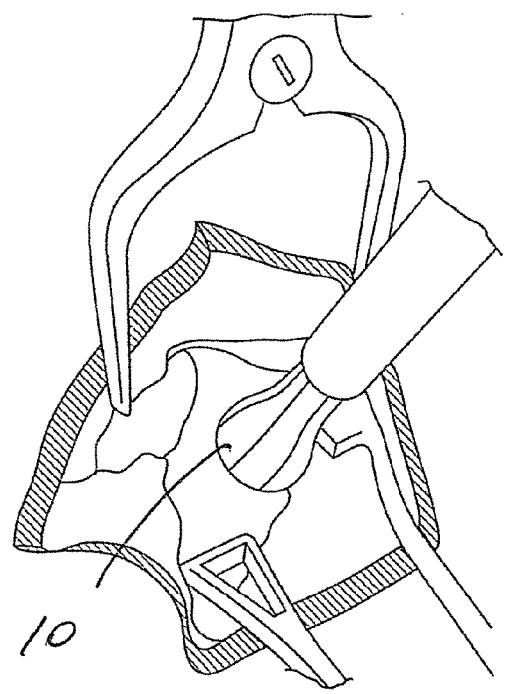

Any suitable electroporation treatment may be applied using the electrodes. Any described sequence of electroporation pulses may be used. Referring in particular to FIG. 2 there is one central electrode and any number, typically from five to eight and in this case six outer needle electrodes.

In one case the electroporation sequence involves a pulse between the inner electrode 11 and all of the outer electrodes 12 to 17. Alternatively, for optimum treatment, a more complicated sequencing regime in which the inner electrode 11 is first pulsed with outer electrodes 12 and 13, then with outer electrodes 13, 14, then 14, 15, then 15, 16, then 16, 17, and then 17, 12.

Electroporation involves higher voltages applied over a short time. This is in contrast to ablation which involves low voltages applied over a long time.

Typical electroporation parameters applied using the needle electrodes in the device of the invention are:
1) Involving Drug
A voltage of 800-1300 V/cm, with eight 100 microseconds pulses at a frequency of between 1 Hz and 5 KHz.
2) Where no drug is used (irreversible electroporation)
A voltage of 1500-2500 V/cm, with 80-200 100 microseconds pulses at a frequency of between 1 Hz and 5 KHz.
3) Where the therapeutic is a DNA plasmid
One 100 microsecond pulse of 1300 V/cm followed within 1-5 second by a train of 4 50 msec pulses with a voltage of 30-200 V/cm at a frequency of 1 Hz.

Figure 13:
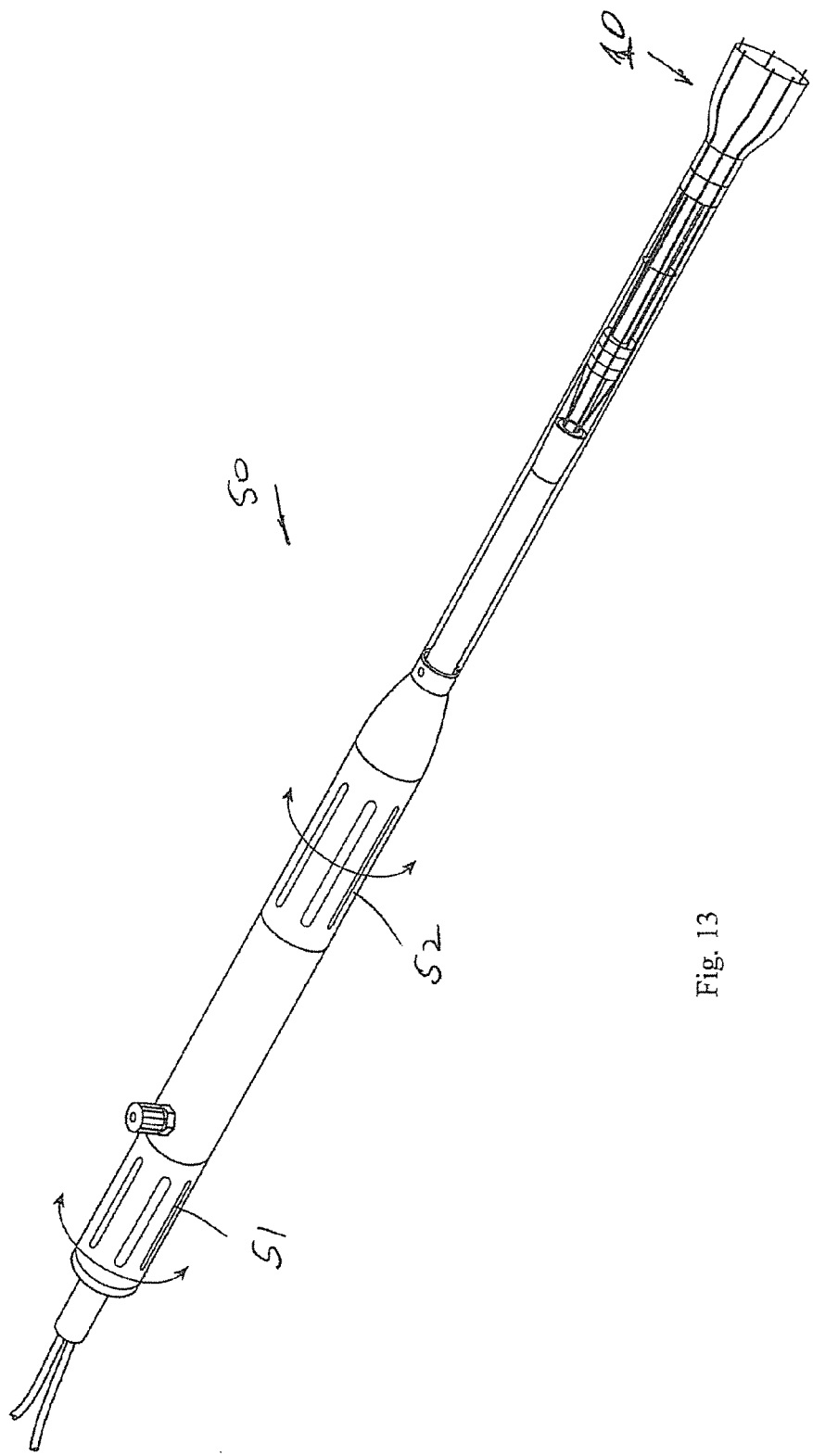
FIG. 13 is a perspective view of one surgical device incorporating the apparatus of the invention.
Figure 14:
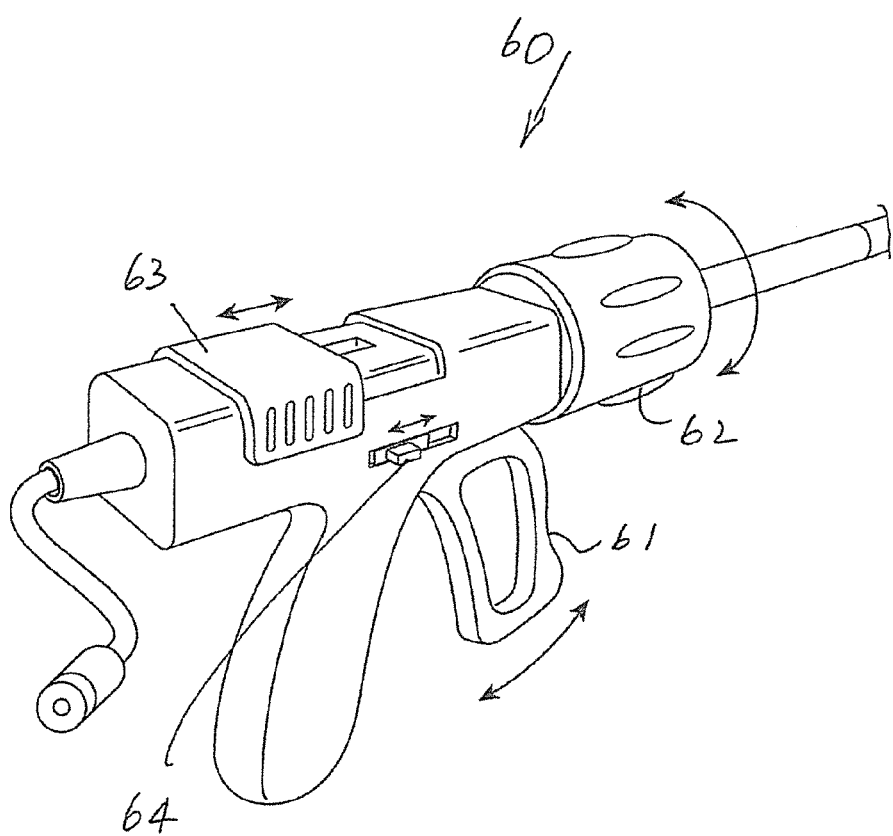
FIG. 14 is a perspective view of another surgical device incorporating the apparatus of the invention.
Figure 15:
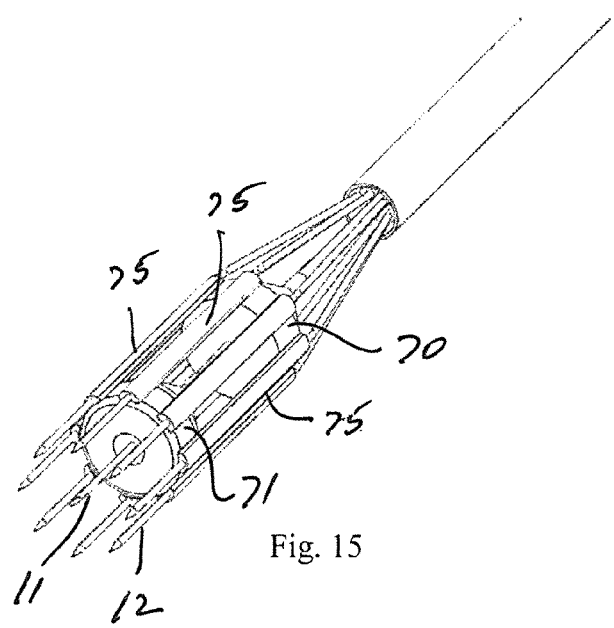
FIG. 15 is an isometric view of another device according to the invention.
Figure 16:
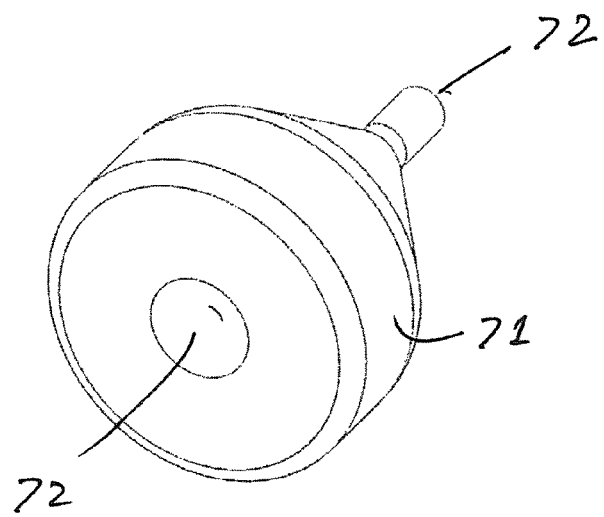
FIG. 16 is an isometric view of a biasing element part of the device of FIG. 15.

The apparatus of the invention may be provided at the distal end of any suitable instrument. For example, as illustrated in FIG. 13 one such instrument 50 may have a proximal handle portion 51, 52 which may be moved, in this case rotated to deploy the suction head 1 and then deploy the needles from the suction head 1. The proximal end of another instrument 60 is illustrated in FIG. 14. In this case there are several operator controls 61, 62, 63, 64 which may be used to operate the various functions of the apparatus from the proximal end.

Referring to FIGS. 15 to 26 there is illustrated another device according to the invention in which parts similar to those of earlier embodiments are assigned the same reference numerals. In this case the biasing means comprises at least one expansile element such as a balloon. In this case there are two balloons 70, 71 which are axially spaced-apart along the suction head for improved control of operation. Each of the balloons 70, 71 has a central hole 72 through which the central needle 11 can pass when the balloons are in both the expanded and retracted configurations. Circumferentially spaced-apart sleeves 75 are provided around the periphery of the head to accommodate axial movement of the second needles and movement of the second needles between the radially retracted and radially expanded configurations.

Figure 27:
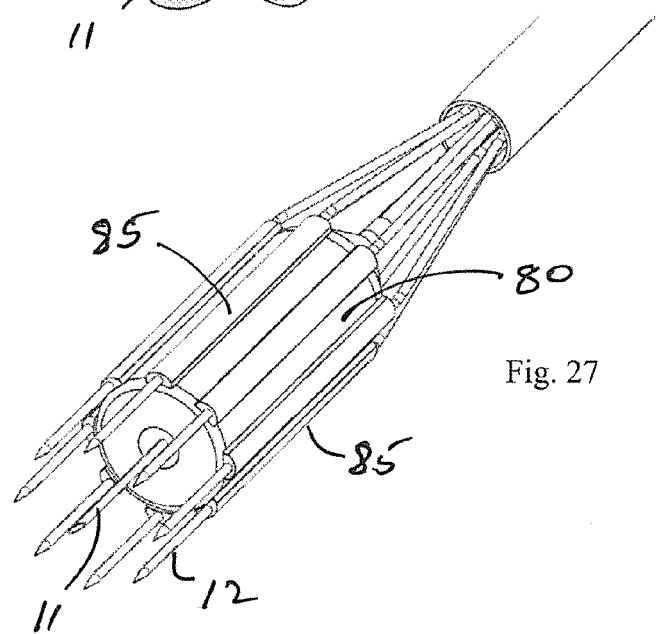
FIG. 27 is an isometric view of a suction head and needles of another device f the invention.
Figure 28:
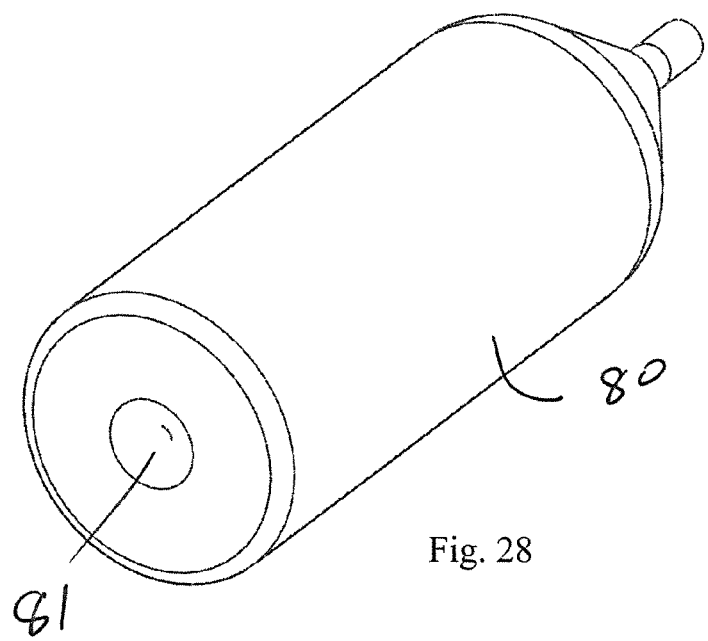
FIG. 28 is an isometric view of a biasing element part of the device of FIG. 27.
Figure 29:
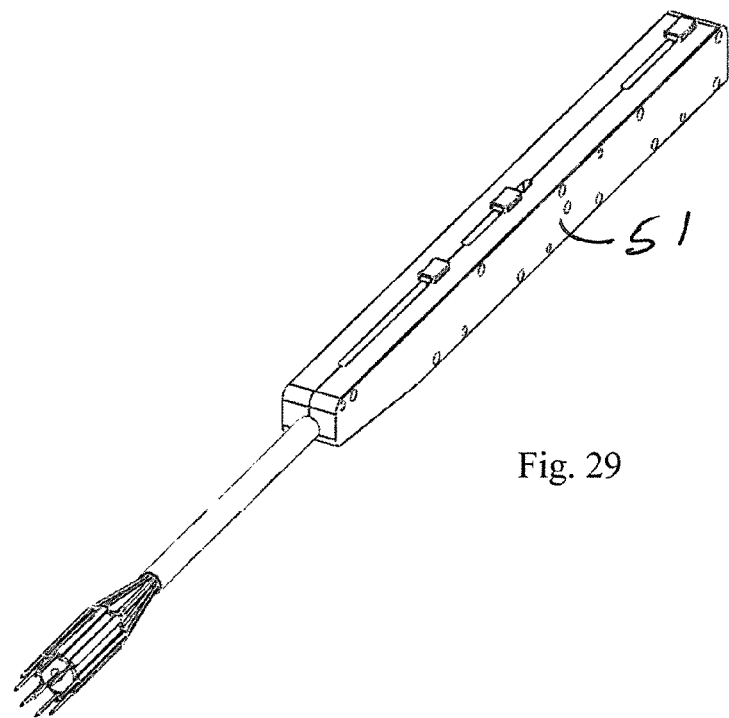
FIG. 29 is a view of the device of FIG. 27 including an operating handle.
Figure 30:
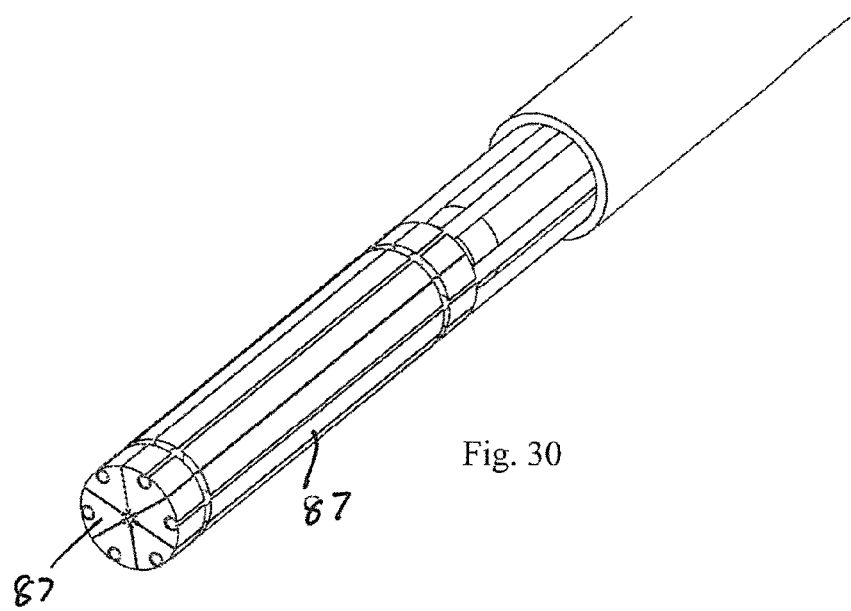
FIG. 30 is a view of the device of FIG. 27 with segmented biasing elements in a retracted configuration.
Figure 31:
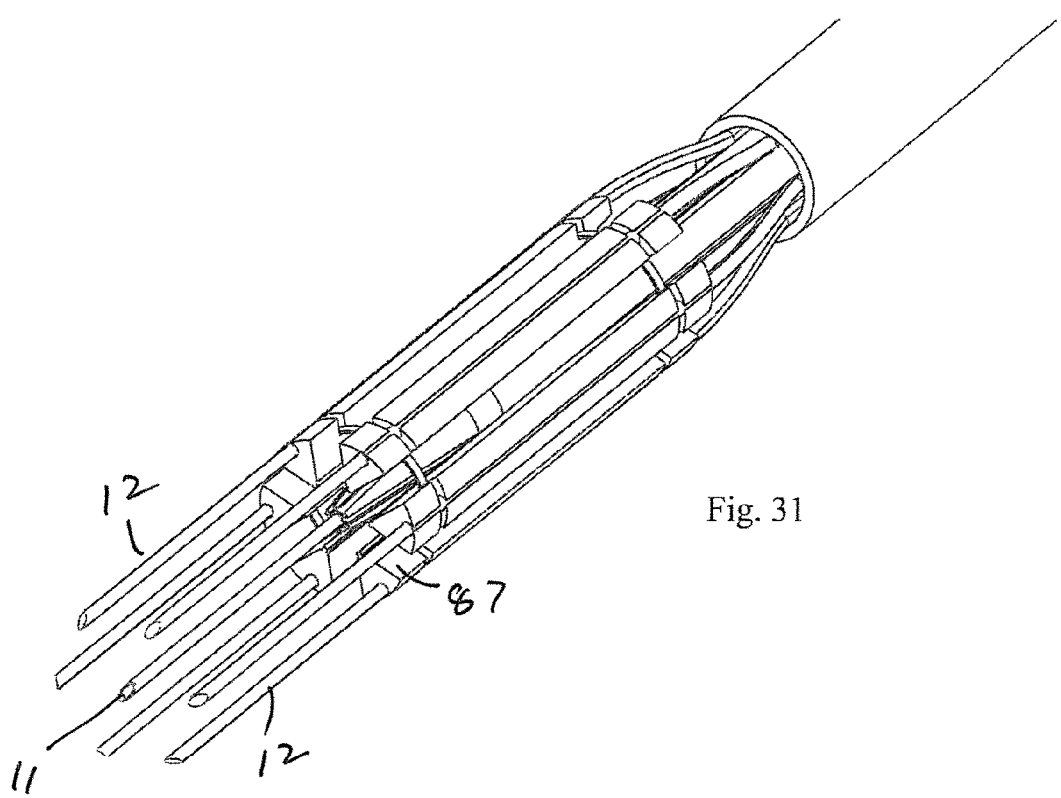
FIG. 31 is a view similar to FIG. 30 with the biasing elements expanded and the needles extended.
Figure 32:
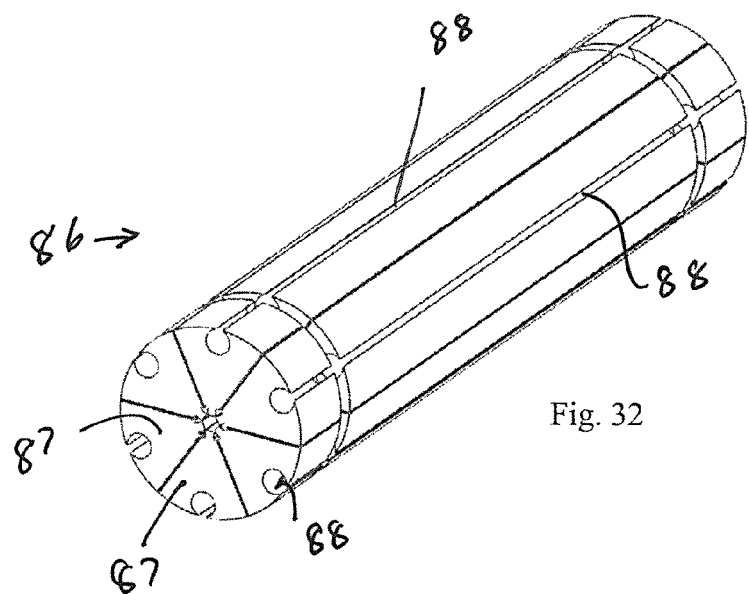
FIGS. 32 and 33 are isometric views of the biasing elements of FIG. 31 in retracted and extended configuration.

Referring to FIGS. 27 to 29 there is illustrated another device according to the invention in which parts similar to those of earlier embodiments are assigned the same reference numerals. In this case the biasing means comprises a single expansile element 80 such as a balloon which has a central hole 81 through which the central needle can pass when the balloon is in both the expanded and retracted configurations. Circumferentially spaced-apart sleeves 85 are provided around the periphery of the head to accommodate axial movement of the second needles and movement of the second needles between the radially retracted and radially expanded configurations.

Figure 33:
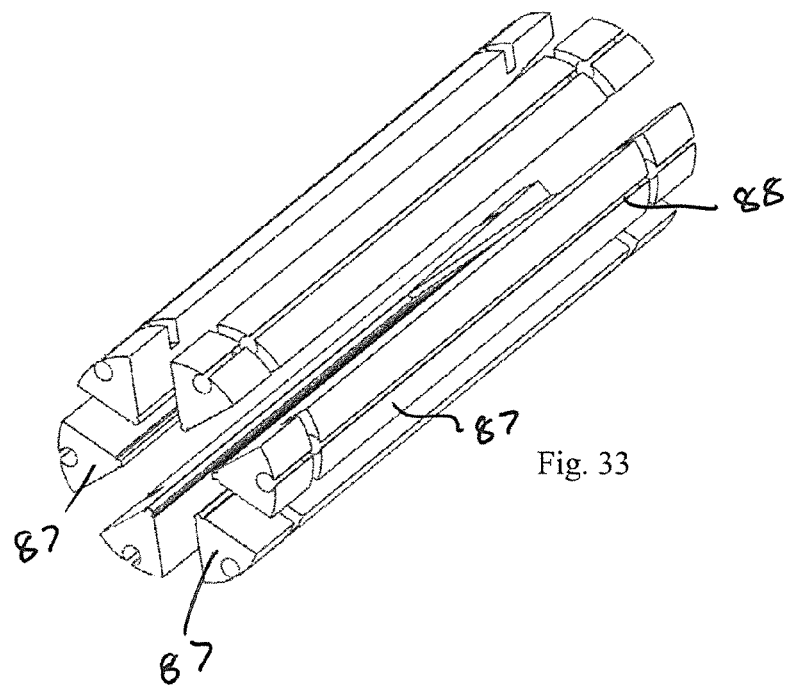
Figure 34:
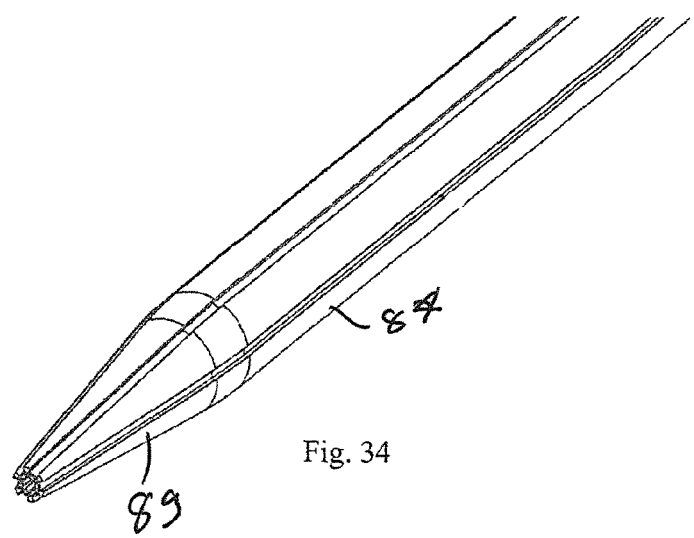
FIG. 34 is an isometric view of a portion of a device of the invention with a tapered distal tip.
Figure 35:
FIGS. 35 and 36 are views of another device according to the invention with needles retracted (FIG. 35) and extended axially (FIG. 36)
Figure 36:
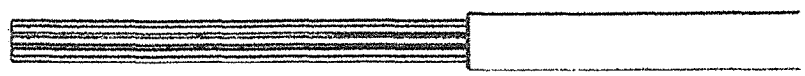
Figure 38:
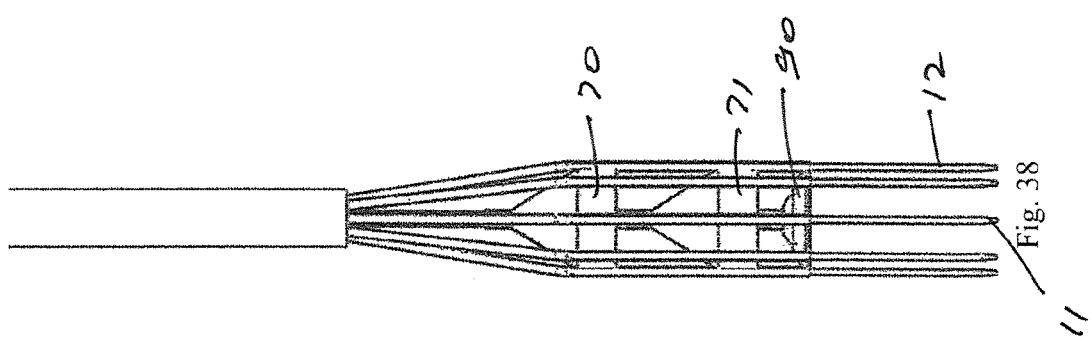
FIGS. 37 and 38 illustrate a device of the invention with another biasing system.
Figure 37:
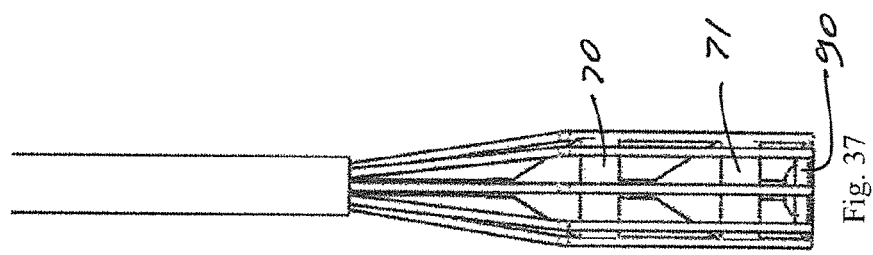
Figure 39:
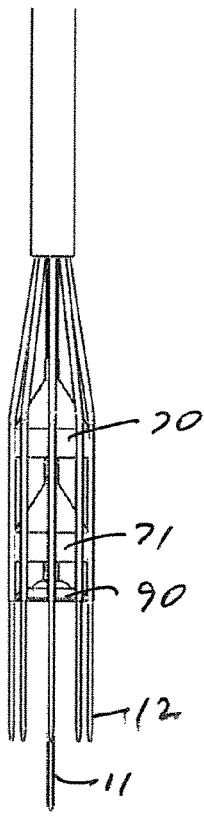
FIG. 39 is a view similar to FIG. 38 with a central needle extended beyond peripheral needles.
Figure 40:
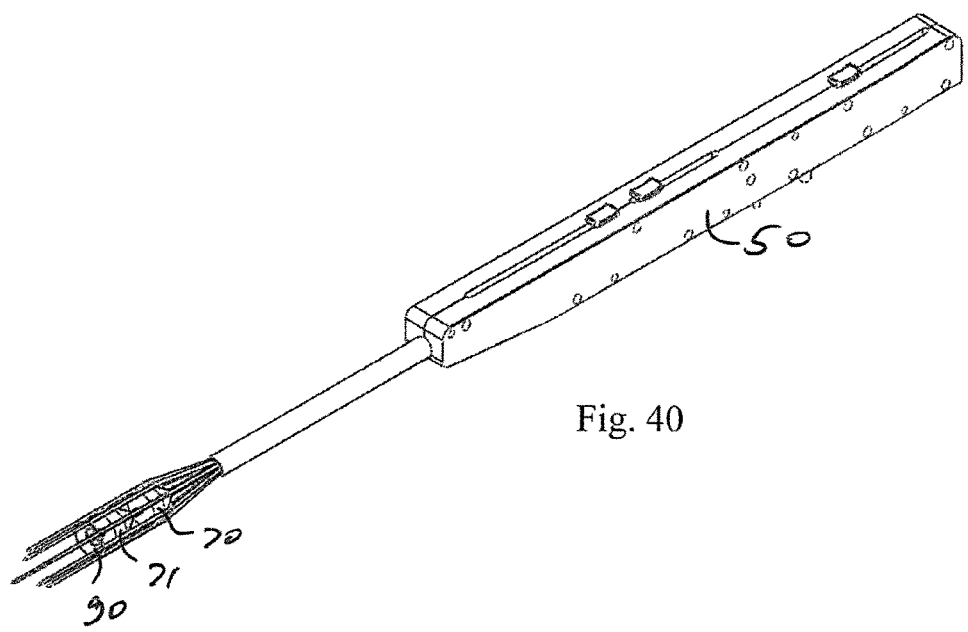
FIG. 40 is a view of the device of FIGS. 387 to 39 with an associated operating handle.
Figure 41:
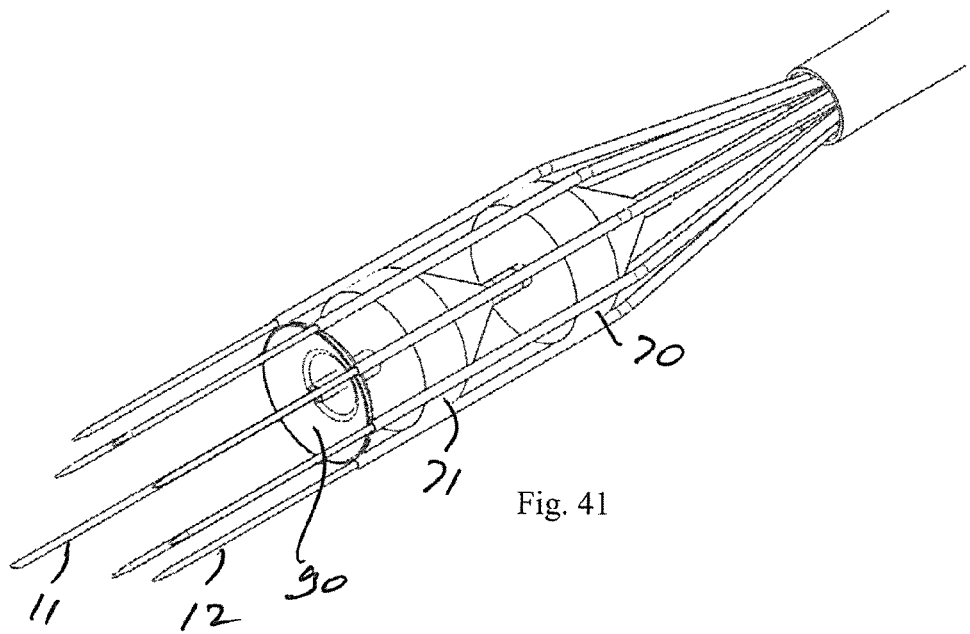
FIG. 41 is an isometric view of another device according to the invention.
Figure 42:
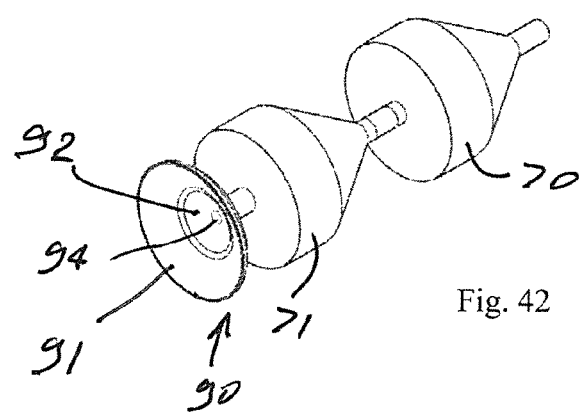
FIG. 42 is an isometric view of biasing element parts of the device of FIG. 41.
Figure 43:
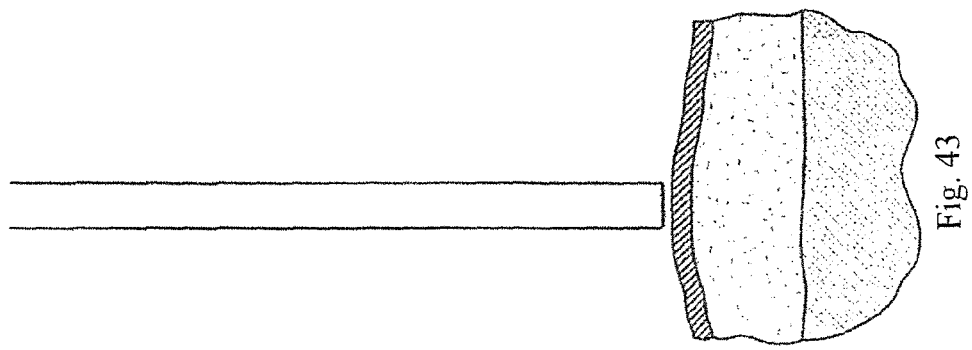
FIGS. 43 to 47 illustrate the device of FIGS. 37 to 42, in use.
Figure 44:
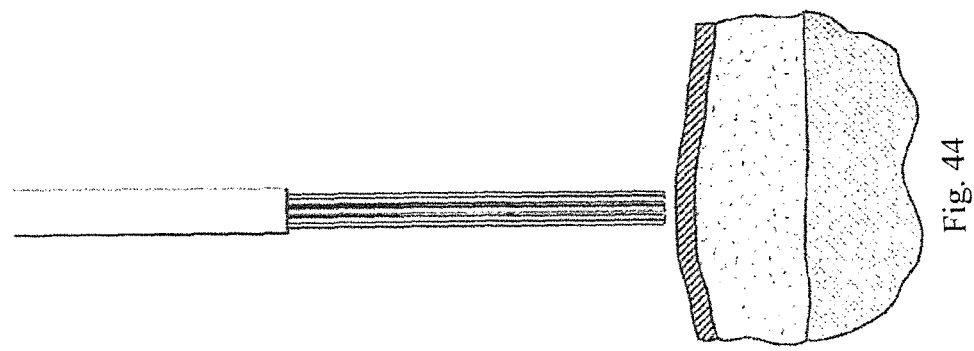
Figure 45:
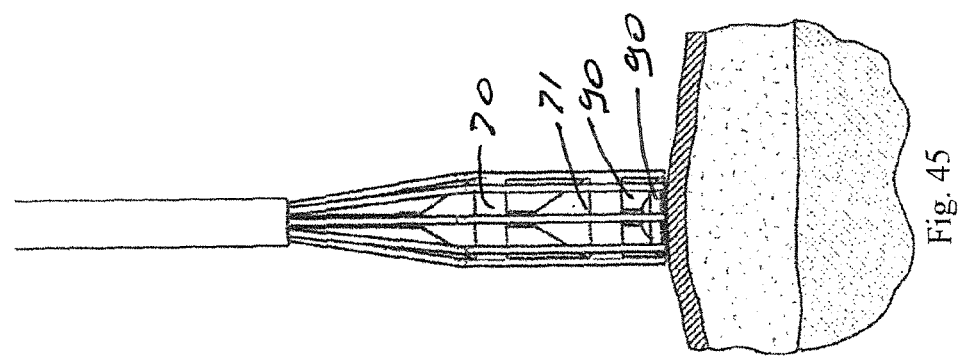
Figure 46:
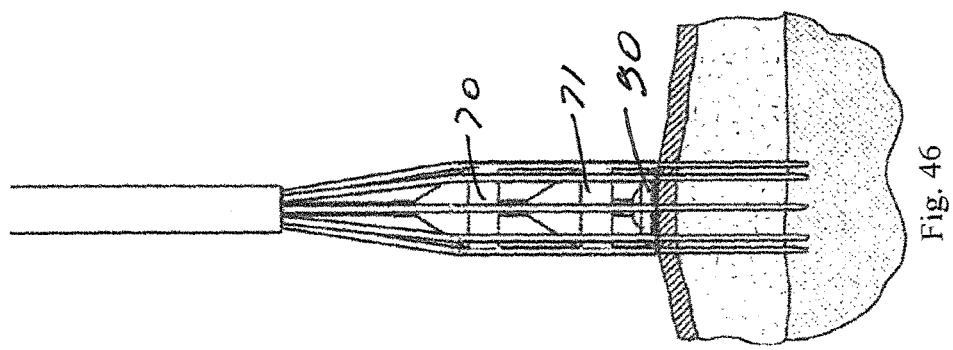
Figure 47:
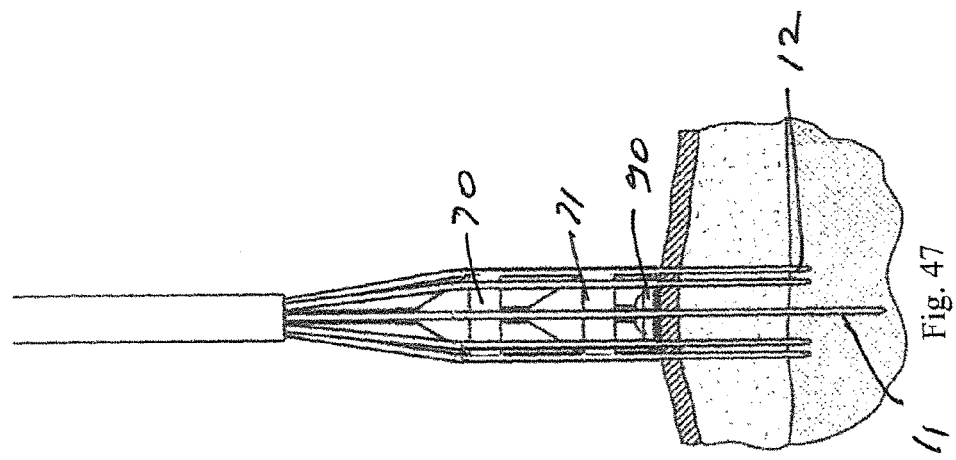

Referring to FIGS. 30 to 34 there is illustrated another device according to the invention in which parts similar to those of earlier embodiments are assigned the same reference numerals. In this case the biasing means comprises a central element 84 around which are connected a number of arms 87 (typically five or more). The segments or arms 87 are normally in a retracted configuration. The arms 87 are moved radially outwardly by pushing the central element 84 axially through the centre of the head. A distal tip 89 of the central tip 84 is tapered (FIG. 34) to facilitate entry and passage through the head to splay apart the arms 87. The arms are expanded in this way through a connection in the handle which levers the arms 87 outwards into an expanded position (FIG. 33). At this stage the second needles can be deployed through a channel/cavity line 88 within each arm (FIG. 31) and inserted into the tissue. The arms 87 may be adapted to return to the retracted configuration when the central element 84 is retracted.

Referring now to FIGS. 35 to 47 there is illustrated another device according to the invention in which parts similar to those of earlier embodiments are assigned the same reference numerals. In this case there are two balloons 70, 71 which are axially spaced-apart along the suction head for improved control of operation. Each of the balloons has a central hole 72 through which the central needle can pass when the balloons are in both the expanded and retracted configurations. Circumferentially spaced-apart sleeves 75 are provided around the periphery of the head to accommodate axial movement of the second needles and movement of the second needles between the radially retracted and radially expanded configurations. In this case there is also a distal cup shaped element 90 which facilitates gripping onto tissue. The cup-shaped element 90 comprises an outer part 91 and an inner part 92. The outer part 91 is more flexible than the relatively stiff inner part 92. The inner part 92 provides enhanced strength whilst the outer part 91 facilitates collapse and expansion on movement between the retracted and expanded configurations. The inner part may for example be of a relatively stiff polycarbonate material or pebax and the outer part of a more flexible polyurethane material. The outer part also has a hole 94 through which the central needle may extend.

The invention provides a thoracoscopic device for use in the electropermeabilisation treatment of lung cancer specifically but also has application to other laparoscopically accessible tumours. Lung cancer is not adequately addressed by existing therapies, and offers a significant opportunity in which to present a minimally invasive tumour resolution method. Currently between 80%-85% of patients are deemed unsuitable for surgical treatment. In contrast to other methods such as radio frequency ablation (RFA), e.g. Leveen needle, radiotherapy or surgery the use of electropermeabilisation is uniquely designed to use electrical energy to make the cell membrane temporarily porous whereas other ablation methods such as RFA elicit a therapeutic effect by using heat to denature and immediately destroy all surrounding tissues.

An instrument according to the invention has a proximal end and a distal end and comprises a flexible suction cup at the distal end thereof. The distal cup comprises an array of small diameter needles (typically with a diameter between 0.1 and 0.2 mm) which are used to deliver electroporation treatment. The suction cup head (typically of a diameter between 2 cm and 3 cm) has a collapsed delivery configuration and an expanded deployed configuration. At the treatment site, the suction cup is deployed and placed on the tumour tissue. Suction is used to grip the appropriate area of tissue. The electroporation needles are then deployed and extended to a depth of typically between 1 cm and 3.5 cm into the tissue to be treated. The array of needles comprises a central needle and an edge group comprising a plurality of peripherally spaced-apart needles. The central needle in this case forms the positive electrode and the edge group of needles form the negative electrodes for delivery of electroporation.

The instrument may be delivered to a site of interest such as the lung through a patient's chest wall.

In one case the instrument is a laparoscope and the central core of the laparoscope contains the suction cup head. A proximal handle on the laparoscope may be used to deploy the electroporation needles.

The primary advantages of the device of the invention are:
1. Keyhole procedure:
2. Excellent efficacy
3. Minimal side effects
4. Immunomodulatory:
5. Rapid
6. Control of tissue engagement and needle deployment through the use of vacuum The thoracoscopic system of the invention delivers electrodes in a controlled and targeted manner to tumour tissue. Vacuum is used at the head of the device to grip the tissue and facilitates the impaling of the needle electrodes into the adjacent tumour tissue. This also minimises the trauma caused by the needles and reduces the risk of air leaks post treatment. The vacuum has another important feature critical to supporting the clinical efficacy of the treatment. The applied vacuum can cause the tumour interstitial pressure to reduce from positive to negative (mmHg) and thereby allow better drug distribution within the tumour.

An electrical field is generated between the electrodes around the tumour, which ensures the tissue becomes porous allowing passive diffusion of a locally present chemotherapeutic macromolecule, such as bleomycin or cisplatin. Absorption occurs only in the area that has been electroporated and therefore is targeted to the tumour, leaving surrounding healthy tissues unaffected. One of the significant advantages of the system is that healthy cells and tissues surrounding the tumour can be treated to a greater degree than conventional ablation methods such as radiotherapy and radiofrequency ablation. The difference between delivering electroporation which causes tissue to become porous and on its own is not destructive and radio frequency ablation which essentially uses heat to immediately destroy the surrounding tissues is an important distinction. In the invention, the electroporation electrodes can be placed visually within a few seconds. From a treatment time perspective electroporation take less than 1 msec or 0.001 second whereas RFA can take between 10-20 minutes i.e. 1200 seconds—a 1.2 million fold difference.

In addition, in terms of electrode positioning the use of conventional RFA needles is carried out under radiological guidance with critical importance being given to placement near arteries or blood vessels. In complete contrast, the device of the invention is positioned under visual guidance via video with placement achieved in a matter of seconds.

The impact immunologically is one of the most important benefits of treatment with the electroporation device of the invention. Surgery does not elicit an immunological reaction as the tumour tissue has been removed from the patient; rather the physical stress of the procedure is in most cases immunosuppressive. Similarly with treatment such as RFA and radiotherapy the local effect is immunosuppressive rather than facilitating a boost in the immune response against the cancer. Also RFA thermally destroys the tumour tissue and associated antigens reducing the ability for the immune system to benefit as the tumour dies. With the electroporation system of the invention there is a beneficial immune response, which we have demonstrated, in murine models to increase immune engagement against the cancer through an increase in the presence of antigen presenting cells (APCs) e.g. dendritic cells and a corresponding boost in the level of CD8+ cytotoxic t cells. We have demonstrated a reduction in lung metastasis after treatment in murine models with the electroporation approach of the invention.

Figure 48:
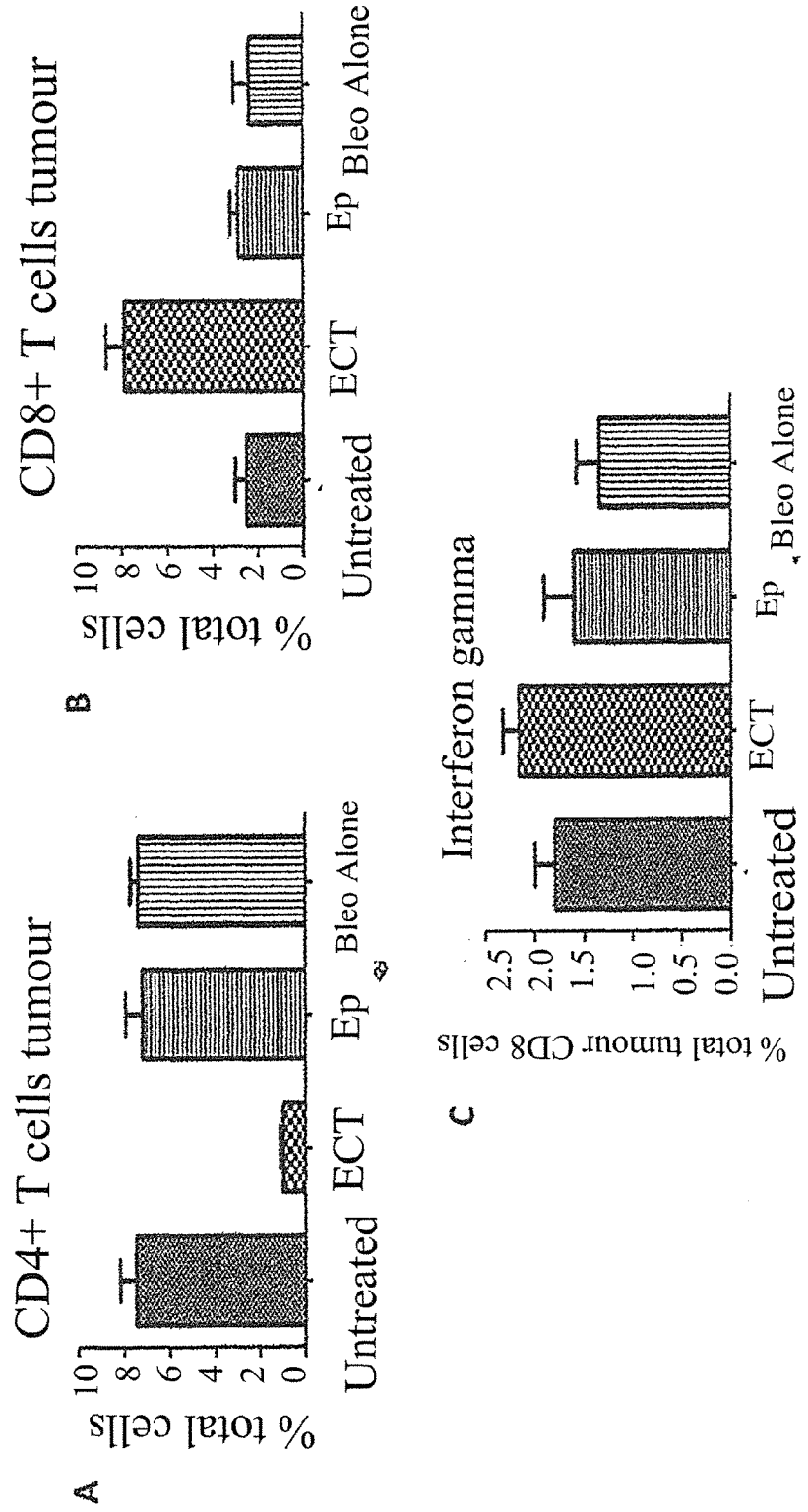
FIG. 48 are bar charts illustrating FACS immune profiling of electrochemotherapy treatment of lung cancer in a murine CMT lung tumour model. A. Down regulation of CD4/CD25$^+$ T-regulatory cells in the electroporated+cisplatin treated (ECT) tumour. B. An increase in CD8$^+$ T effector cells in ECT treated tumours. C. Cytototoxic CD8$^+$ response as indicated by the % of CD8 doubled stained for interferon gamma (cytotoxic marker)

FIG. 48 are bar charts illustrating FACS immune profiling of electrochemotherapy treatment of lung cancer in a murine CMT lung tumour model. A. Down regulation of CD4/CD25$^+$ T-regulatory cells in the electroporated+cisplatin treated (ECT) tumour. B. An increase in CD8$^+$ T effector cells in ECT treated tumours. C. Cytototoxic CD8$^+$ response as indicated by the % of CD8 doubled stained for interferon gamma (cytotoxic marker).

Figure 49:
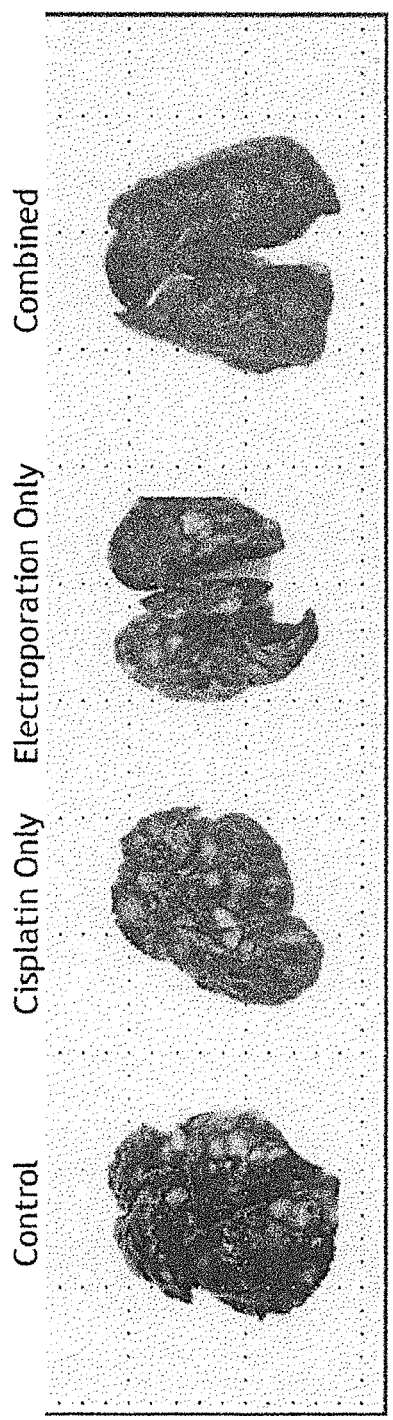
FIG. 49 are images illustrating immuno-modulation comparisons in a lung metastatic model of control (no treatment), cisplatin, electroporation alone versus treatment group treated with a combination of electroporation and cisplatin. Images of murine lung metastasis (Feketts Assay—tumours stain white) demonstrate that tumour resolution in situ due to electroporation and cisplatin treatment is effective at inhibiting the establishment of lung metastasis.

FIG. 49 are images illustrating immuno-modulation comparisons in a lung metastatic model of control (no treatment), cisplatin, electroporation alone versus treatment group treated with a combination of electroporation and cisplatin. Images of murine lung metastasis (Feketts Assay—tumours stain white) demonstrate that tumour resolution in situ due to electroporation and cisplatin treatment is effective at inhibiting the establishment of lung metastasis.

Some advantages of for the electroporation system of the invention are:
1. Favourably modulates the immune response towards improved immune recognition of tumour associated antigens.
2. Increases the number of dendritic cells (APCs) to the site of the tumour, aiding tumour associated antigen recognition as the tumour decays.
3. Modulates Toll like receptors favourably towards an adaptive immune response to the tumour which can be modulated further through the presence of additional modulators of B7.1/2 cell expression e.g. lactoferrrin or vitamin E analogs.
4. Tumour antigens are left in situ as the tumour decays in contrast to surgery where the tumour is removed completely and RFA where the tumour antigens are denatured following treatment Other advantages and improvements of this invention over existing methods/materials/devices/current state of the art include:

Targeted Delivery: Drug absorption is localised to the area treated by the device, only a fraction of drug used compared to standard (therefore less side effects for patient).

Healthy Tissue: Studies to date indicate that healthy tissue is significantly less affected than tumour tissue allowing wider margins around the tumour to be treated, thereby decreasing the potential risk of recurrence.

Repeatable: Treatment can be delivered multiple times if required

Minimally invasive and non-toxic: The dose of drug used is less than 1% of that used in conventional chemotherapy. Endoscopic application allows for a greater number of patients to receive treatment.

Unlike other ablation methods the method of cell death is primarily apoptotic, non necrotic response.

New therapeutics: Future potential for the device to be used for gene therapy and combination with antibody therapies.

The electroporation treatment can be applied quickly reducing the time for recovery from anaesthetic compared to normal general surgery.

The technology is complementary to existing therapies, is easy to perform and has an economic cost savings advantage.

The needles may be deployed via a twisting mechanism in the handle section. Preferably the treatment head is flexible and will be delivered in the first stage in an embedded/collapsed stage in the scope and opens out into a 'suction cup shape' fully once inside the body.

In practice the treatment head is opened to prepare for tissue contact once inserted into the body (A). Once the suction cup has grasped the tissue (B) the needles are deployed through the cup (C) into the underlying tissue. The central needle can be deployed independently (D). This has the advantage of gripping the tissue for the surgeon while the electrodes are deployed into the tumour.

FACS immune profiling of electrochemotherapy treatment of lung cancer in a murineCMT lung tumour model. A. Down regulation of CD4/CD25$^+$ T-regulatory cells in the electroporated+cisplatin treated (ECT) tumour. B. An increase in CD8$^+$ T effector cells in ECT treated tumours. C. Cytototoxic CD8$^+$ response as indicated by the % of CD8 doubled stained for interferon gamma (cytoxic marker).

Immuno-modulation comparisons in a lung metastatic model of control (no treatment), cisplatin, electroporation alone versus treatment group treated with a combination of electroporation and cisplatin. Images of murine lung metastasis (Feketts Assay—tumours stain white) demonstrate that tumour resolution in situ due to electroporation and cisplatin treatment is effective at inhibiting the establishment of lung metastasis.

The procedure is conducted with the patient under general anaesthetic in a surgical theatre. The tumour would previously have been staged radiologically (CT/PET scans) to assess its location, volume and overall distribution.

The treatment follows an established VATS (video assisted thoracoscopic surgery) procedure. The instrumentation for VATS includes the use of a camera-linked to a 5 mm or 10 mm fiber-optic scope. Unlike with laparoscopy, carbon dioxide insufflation is not generally required with VATS due to the inherent vault-like shape of the thoracic cavity. However, lung deflation on the side of the chest where VATS is being performed is a must to be able to visualize and pass instruments into the thorax; this is usually effected with a double-lumen endo-tracheal tube that allows for single lung ventilation or a bronchial blocker delivered via a standard single-lumen endotracheal tube.

The device of the invention is inserted through a 10 mm trocar access port and brought into position near the site of the tumour. The tumour location is targeted visual using the video camera and with knowledge of the radiological staging.

Once in position the treatment head is expanded to its full size and placed onto the lung tissue. Gentle pressure pressing the device against the tissue is applied and the vacuum port activated. A pressure of between 0 and 700 mmHG is employed to grip the lung tissue and facilitate reducing the tumour interstitial pressure—thereby aiding drug access and circulation within the tumour.

The needles are deployed from the outer rim and the central needle. The central needle is employed to deliver the electroporation pulse and to inject the therapeutic agent into the tumour.

Once the therapeutic agent has been injected the electroporation pulses are delivered via a generator. The needles may be deployed deeper into the tissue after the first set of electroporation pulses and the procedure repeated in steps as the device needle progress deeper into the tissue. The needles may be coated behind the needle tip to minimize the current delivered into the tissue. In this instance the electrical field is only generated around the tip of the treatment head needles and not along the full length.

The needles may be lubricated to facilitate tissue insertion and minimize the force required for their deployment.

The needles may be retracted after application and the treatment head repositioned to ensure the full surface area of the tumour has been treated.

The central needle is of a higher gauge that the surrounding needles on the outer rim of the treatment head. The narrower gauge needles minimize trauma to surrounding healthy tissue and in the lung reduce the likelihood of air leaks after treatment.

Also the central needle can monitor the tissue impedance and provide feedback to the generator of its presence within tumour or healthy tissue. The impedance of tumour tissue has a characteristic frequency reading and is also adjusted after electroporation pulses are delivered. Impedance measurement readings/feedback from the central needle can indicate to the operate the presence within tumour tissue, its effective electroporation and if the needle has penetrated through the tumour to healthy tissue i.e. the needle has fully penetrated through the tumour.

Additional immune modulating agents may be used to further facilitate the immune enhancing effect of electroporation with the device of the invention. These immune modulating agents would typically be added in the days before treatment either via dietary supplements or as a direct intratumoural injection before treatment of at the time of electroporation. Such agents include antibodies such as ipilimumab, ICOS, OX40, PD1 and PD-L. They facilitate the immune response through direct anticancer action and through upregulating B7/1 and B7/2 cell surface expression (which is critical for antigen presentation to antigen presenting cells such as dendritic cells).

Expandable treatment head

Vacuum to grip tissue and reduce tumour interstitial pressure

Coating on needles to control volume of electrical field generated

Immunomodulation as outlined above

Positioning via camera and via impedance measurements on central needle

Lung cancer is the leading cause of cancer-related mortality in both men and women in the developed world. There are over 1.2 million new cases annually worldwide and 1 million deaths (World Health Organisation, WHO). The prevalence of lung cancer is second only to that of prostate cancer in men and breast cancer in women. Most patients who develop lung cancer have been smokers and have smoking-related damage to the heart and lungs, making aggressive surgical or multimodality therapies less viable options.

Conventional treatment for lung cancer includes surgical intervention, which remains the only effective potentially curative treatment (for early stage cancers), chemotherapy, radiotherapy and new treatment modalities such as radiofrequency ablation or use or biological agents such as bevacizumab/avastin. However, despite all the recent advances in the treatment of lung cancer, outcomes are still very poor. Lung cancer accounts for 22% of deaths from cancer and 6% of all deaths (Frost & Sullivan—European Lung Cancer Market Report).

The device of the invention is a novel approach to the treatment of lung cancer. It may be applied via keyhole surgery as a minimally invasive tool in the treatment of both inoperable and operable lung tumours.

The application of electroporation directly to the tumour tissue with the device temporarily permeabilises the tumour cells making them porous and allowing a much greater concentration of chemotherapy drug to be absorbed, thus sparing the healthy tissue and organs of toxicity. Because the concentration of drug absorbed is significantly improved the overall concentration required can be substantially reduced therefore reducing toxicity-associated side effects. One of the main chemotherapy drugs used in treating lung cancer, cisplatin is ideal for this combination treatment and is normally provided to lung cancer patients in a concentration of 60-100 mg/m2 every 3 weeks. This can be reduced to a single dose of 2 mg direct tumoural injection of the drug, a 30-50 fold minimum reduction in concentration.

This approach to tumour ablation has been demonstrated clinically to be effective in malignant melanoma, mercel cell carcinoma, breast cancer, SCC, head and neck cancers and other skin based cancers. An overall objective response rate of 85% has been reported and includes cancers previously unresponsive to treatment.

The reasons for the failure of conventional therapies could be attributed to factors including advanced stage disease at presentation which limits application or effectiveness of treatments, tumour development of drug-resistance, anatomical locations of the cancer that preclude complete excision or ablation, and the presence of undetectable micrometastases at the time of diagnosis or treatment. The other aspect of current anti-cancer therapies is the lack of cancer specificity, resulting in undesirable side effects and therefore, limitation on therapeutic dose. In view of the poor treatment outcomes of lung cancer, the development of alternative and more effective treatment modalities is imperative.

The approach of using electroporation and the device of the invention compared to the standard of care offers benefits to clinicians, patients and healthcare providers. The procedure with the ThoraVe device can be provided in minimally invasive manner (key hole surgery) and the drug concentrations used are significantly lower potentially reducing treatment-associated side effects. In addition the 'hospitalisation' period for the patient can be reduced resulting in significant cost savings to the health care provider.

The electroporation effects are transient and by themselves do not affect tumour growth or tissue function. The poorly permeant chemotherapy drugs by themselves have minimal biological activity but in combination with electroporation their intracellular concentrations are increased several log fold with resulting potent cytocidal effects. Therapeutic influences are therefore confined to the region of the electric field. Cisplatin is such a poorly permeant anticancer drug that is effective and safe in combination with electroporation protocols.

Figure 17:
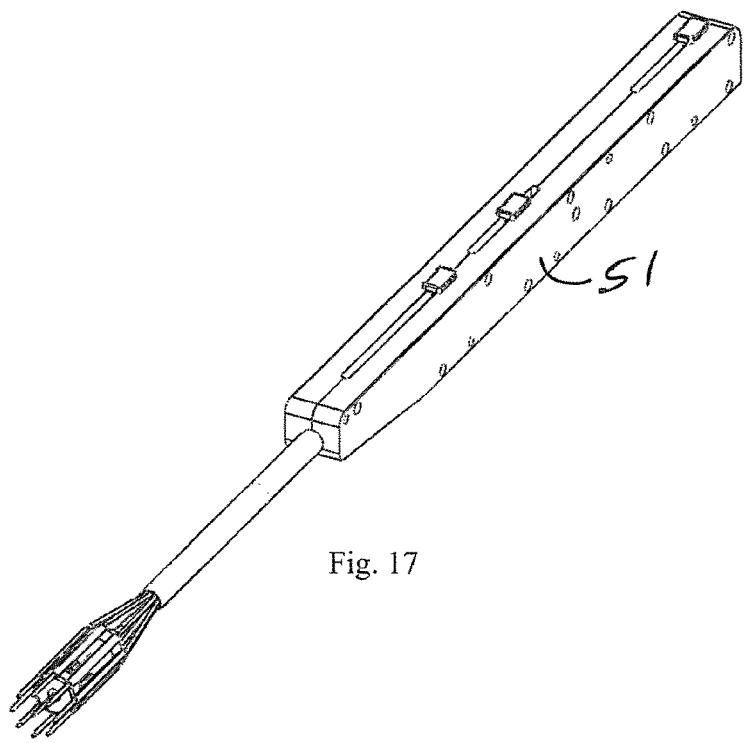
FIG. 17 is a view of the device of FIG. 15 including an operating handle.
Figure 18:
FIGS. 18 and 19 are views of the device of FIGS. 15 to 17 with needles in a retracted configuration.
Figure 19:
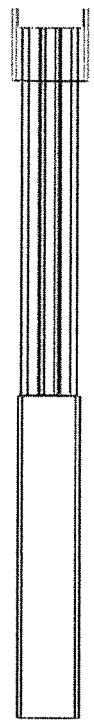
Figure 20:
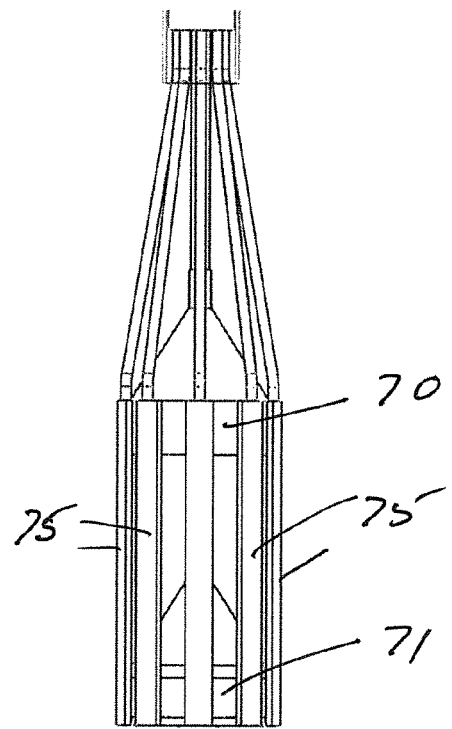
FIG. 20 is a view of the device with the suction head and needles expanded.
Figure 21:
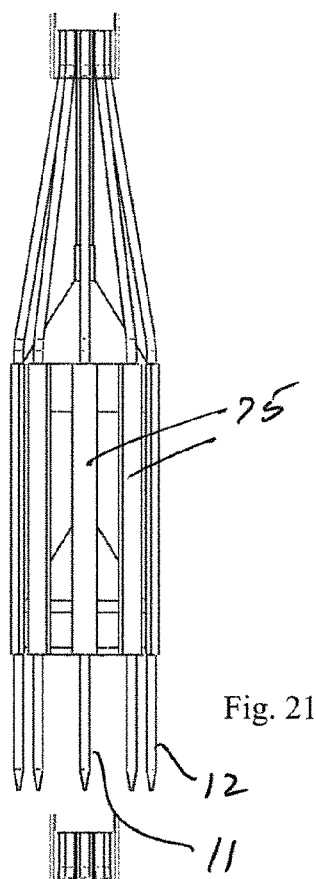
FIGS. 21 to 26 illustrate the device of FIGS. 15 to 20, in use.
Figure 22:
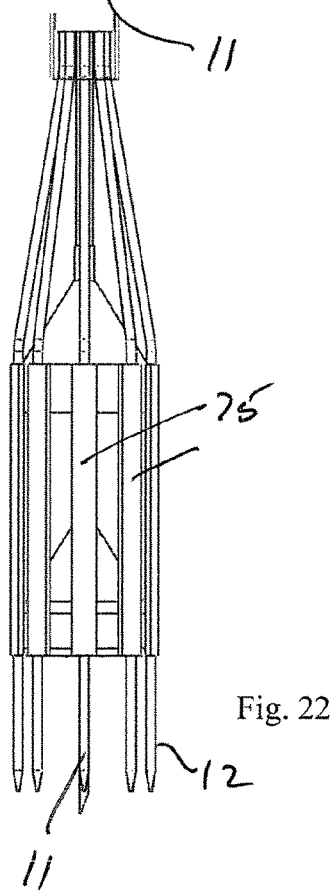
Figure 23:
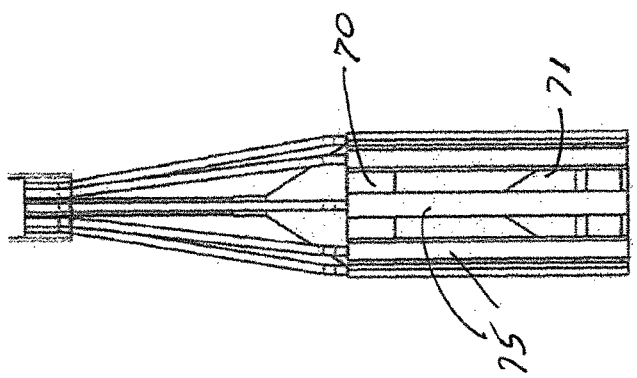
Figure 23:
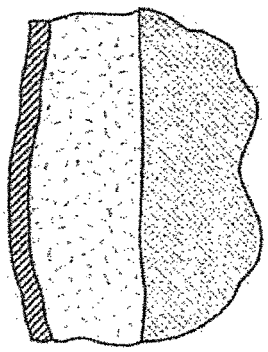
Figure 24:
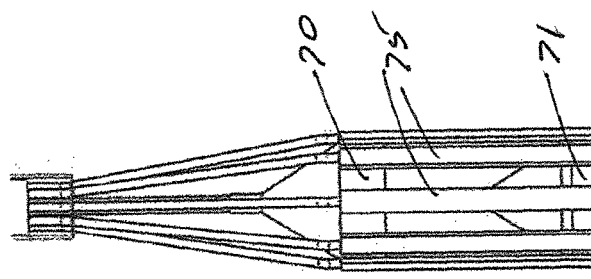
Figure 24:
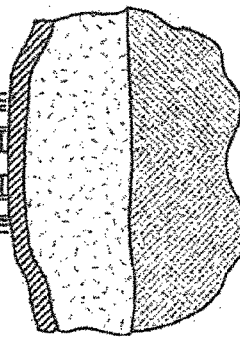
Figure 25:
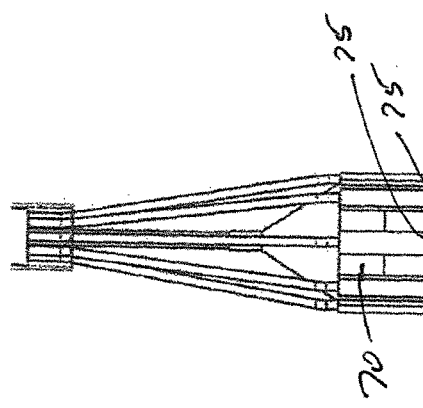
Figure 25:
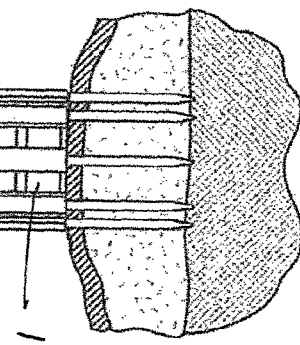
Figure 26:
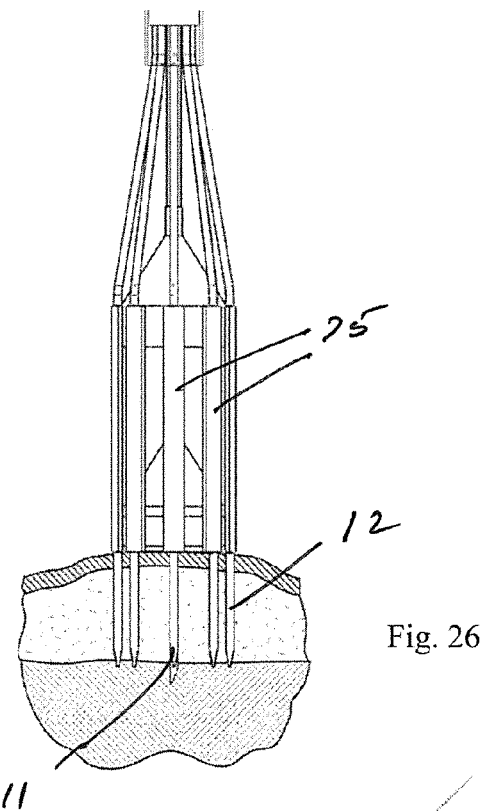

In clinical trials, the use of mild electrical pulses in combination with chemotherapy has proven universally effective in a range of histologically different tumour types, such as malignant melanoma, head and neck cancers and locally recurrent breast cancers. The membrane permeability and cytotoxicity of the chemotherapeutic drugs bleomycin and cisplatin can be dramatically enhanced by electroporation, thus achieving greater antitumour efficacy with reduced systemic drug concentrations and without the associated collateral injury (FIG. 17). Using electrochemotherapy protocols, over 300 patients with unresponsive and inoperable tumour nodules have been treated successfully using skin electrode electroporation at the Cork Cancer Research Centre (CCRC), Mercy University Hospital.

Figure 50:
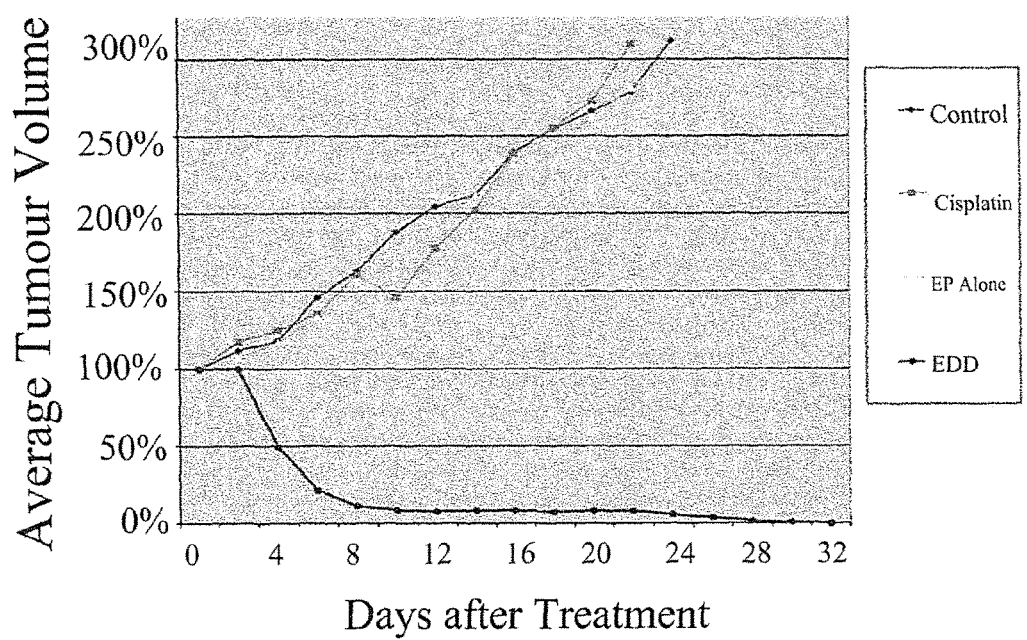
FIG. 50 is a graph presenting in-vivo data: A murine lung cancer tumour model (Lewis Lung Carcinoma) treated with electroporation drug delivery (EDD) showed a complete response over a one month follow up. In contrast the drug alone, electroporation alone and control groups all continued to grow and were culled due to size by day 24 (N=8 per group, starting average tumour volume=150 mm$^3$)

FIG. 50: In-vivo data: A murine lung cancer tumour model (Lewis Lung Carcinoma) treated with electroporation drug delivery (EDD) showed a complete response over a one month follow up. In contrast the drug alone, electroporation alone and control groups all continued to grow and were culled due to size by day 24 (N=8 per group, starting average tumour volume=150 mm$^3$).

To date, the application of electroporation-based therapies has largely been limited to the treatment of externally accessible tumours or tissues due to a reliance on macro needle electrodes. The device of the invention overcomes these limitations, and enables the application of electroporation to both lung cancers and other laparoscopically accessible tumours. Currently a great number of patients are unsuitable for curative surgery due to the invasive nature of the surgical procedure. Despite forming approximately 65 percent of all patients, suitable therapeutics for the elderly remains elusive. The option of employing a minimally invasive procedure to debulk or treat lung tumours offers a large step forward with regard to the options open to the surgeon. If the primary tumour can be managed using an approach that is minimally invasive a significant number of patients with tumours considered inoperable would now have a treatment choice available to them.

Perfusion

Figure 51:
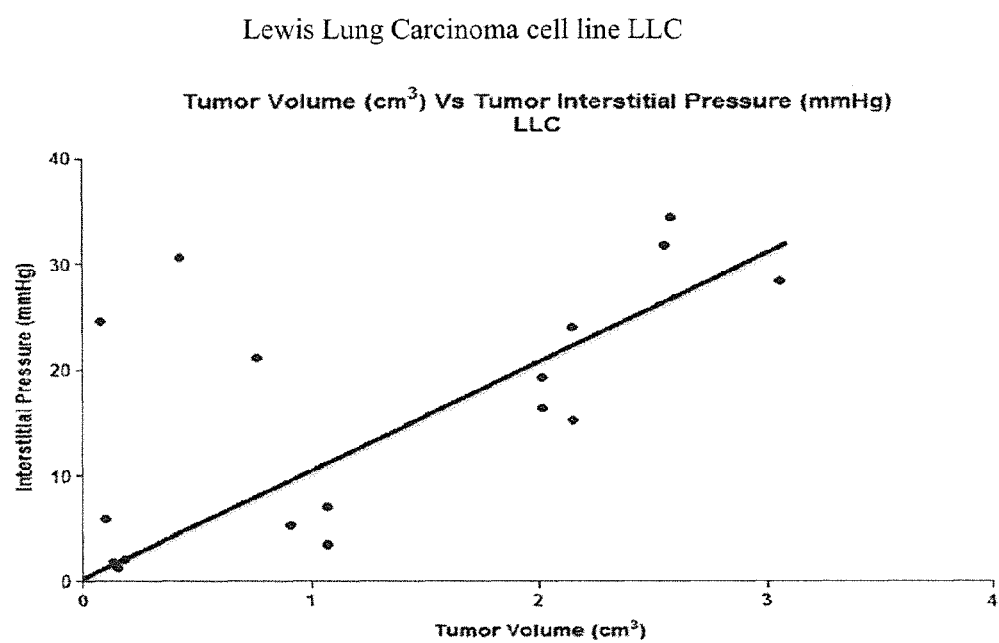
FIG. 51 is a graph which illustrates the correlation between tumour growth and tumour interstitial pressure.

A. One of the physiological impediments reducing the efficacy of chemotherapy relates to the poor diffusion of the drug from the capillaries through to the interstitial spaces surrounding the tumour cells. Poor lymphatic drainage and an irregular vasculature leads to the tumour interstitial pressure increasing with time as the tumour grows. This positive pressure is the opposite of normal tissue where a slightly negative interstitial pressure allows for convection of molecules across the capillaries. See FIG. 51 in which the X-axis represents the tumour volume in cm$^3$, Y-axis represents tumour interstitial pressure readings in mmHg. Each dot represents one TIP reading at a given tumour volume. Linear line represents correlation coefficients between tumour volume and TIP.

Figure 52:
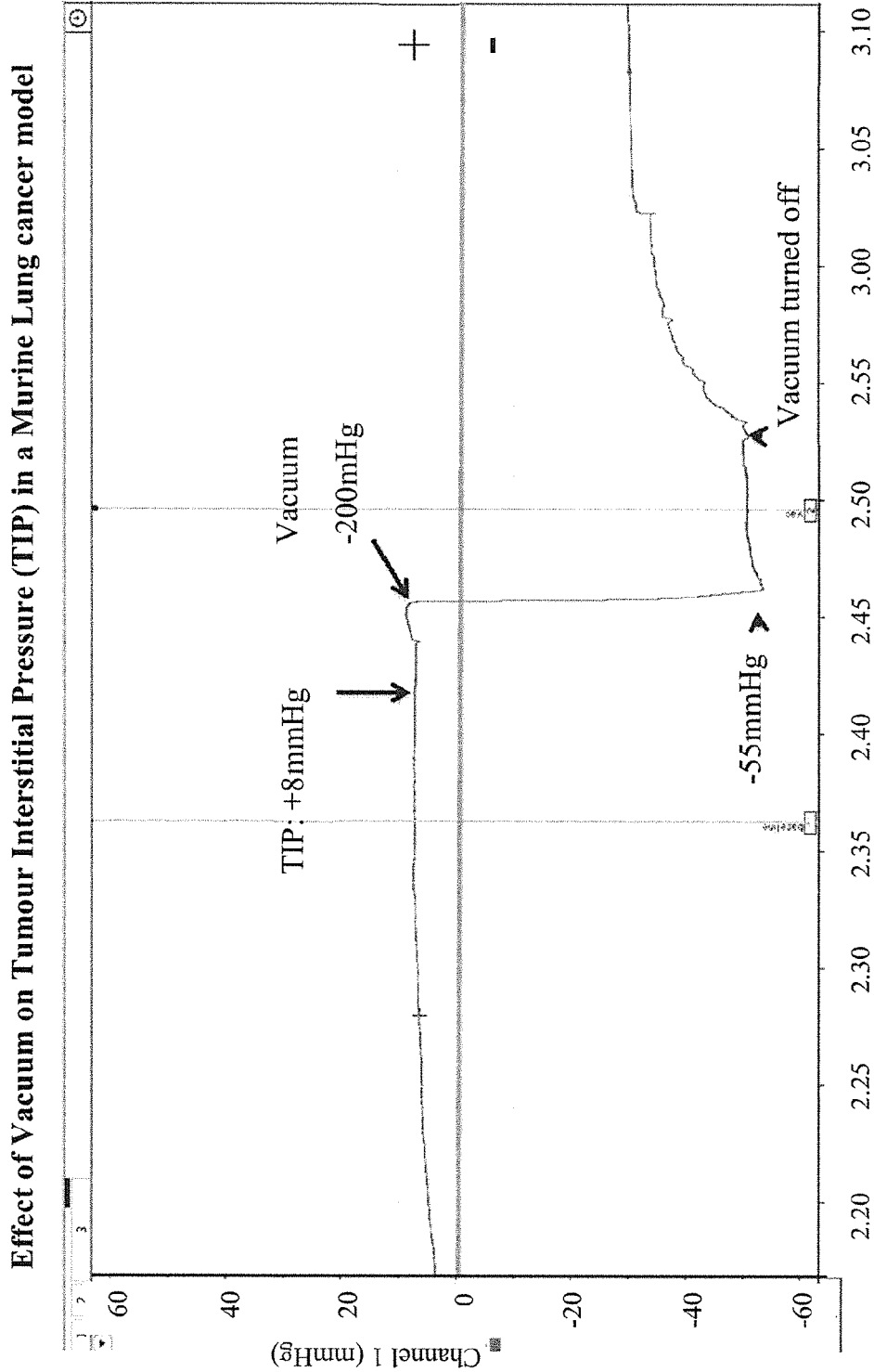
FIG. 52 is a graph which illustrates the effect of vacuum on tumour interstitial pressure (TIP) in a murine mouse model.

B. The positive pressure within the tumour tissue can be immediately negated through the placement of a vacuum directly on the tumour tissue. We achieve this using the device where a vacuum of −200 mm Hg resulted in a decrease of the pressure from a positive +8 mmHg to −55 mmHg within seconds—see FIG. 52 in which internal tumour pressure in mmHg is on the Y-axis with changes over time on the X-axis. As demonstrated, an application of vacuum through the device of the invention immediately results in a reduction of the TIP from +8 mmHg to −55 mmHg. This facilitates better drug perfusion throughout the tumour interstitial spaces (between the cells) by allowing convection of macromolecules from the capillaries to the TIP.

Figure 53:
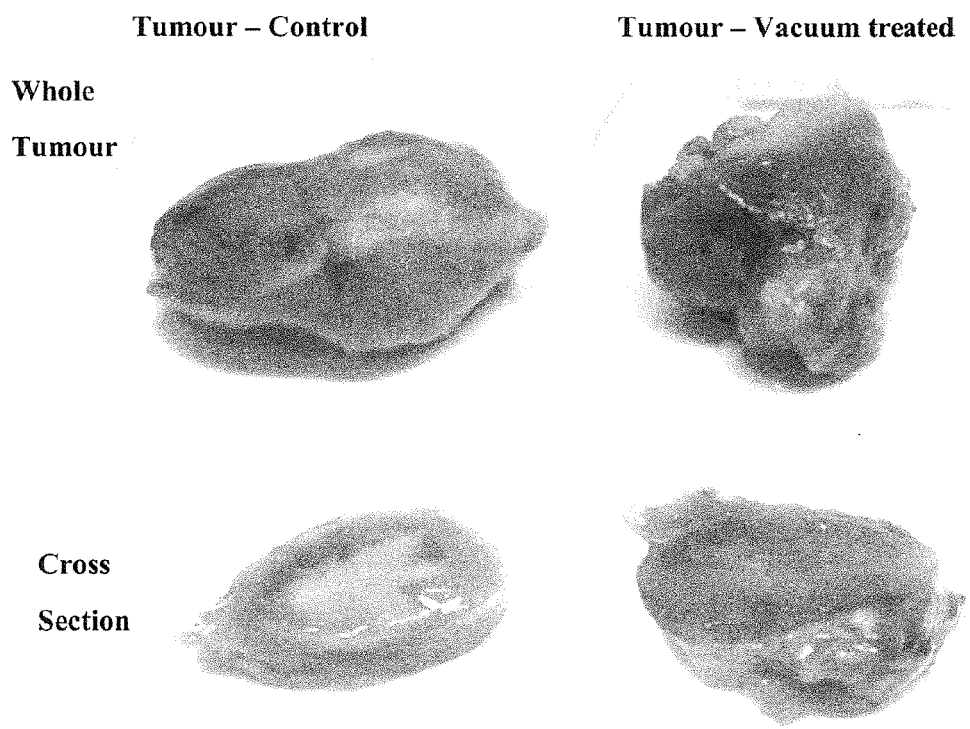
FIG. 53 illustrates the result of an Evans Blue perfusion test.

C. This correction allows for perfusion of the chemotherapy from the capillaries into the tumour tissue. An experiment to confirm the validity of this involves the injection of a blue dye (Evans blue) into the blood supply of a mouse which has a tumour. After 15 mins the organs of the mouse have turned blue but when the tumour is excised and dissected it is clear that only the periphery has absorbed the dye whereas the core of the tumour remains unaffected—due to the high positive interstitial pressure. However when a vacuum is applied to the tumour for 1 minute at 200 mmHg of negative pressure the contrast in drug perfusion into the tumour tissue is clear. Deep permeation of the dye is achieved throughout the tumour tissue, essentially bringing the drug to the door of the tumour cells where electroporation can then open and allow it enter—FIG. 53.

Poration

A. The device of the invention facilitates keyhole surgical access to lung tumours. The device is used as part of a video assisted thorascopic surgery (VATS) procedure where it is inserted into the chest in its closed/collapsed setup to minimise trauma. The diseased lung is collapsed using a bronchial blocker which allows for space to operate inside the chest/lung cavity. Once within the chest space the treatment head is expanded as described above and the treatment head is placed lightly against the lung tissue to be treated. Vacuum is applied through the treatment head to grip and hold the tissue during the procedure and also to reduce the tumour interstitial pressure, which enables full drug perfusion through the tumour.

Figure 54:
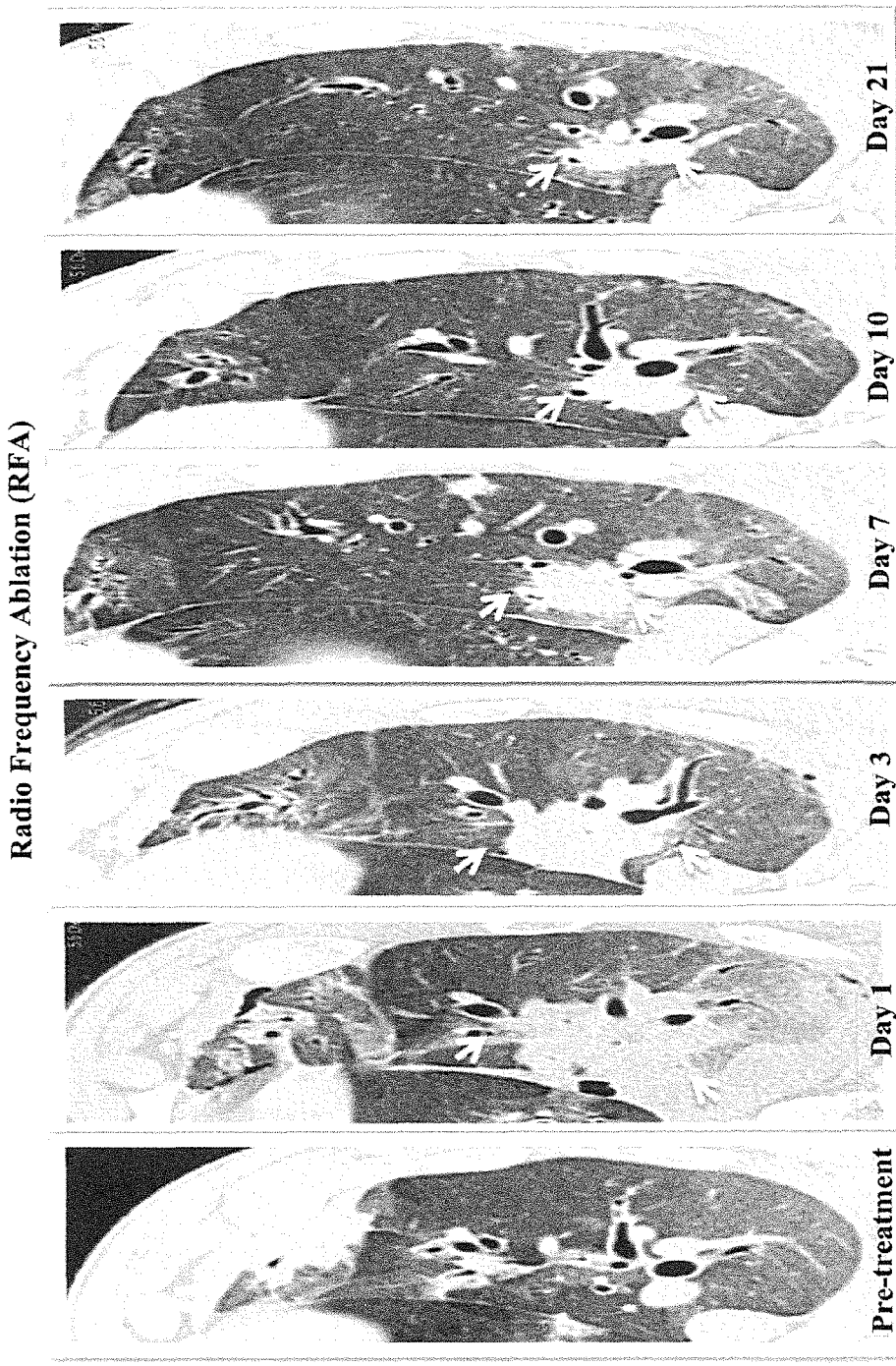
FIG. 54 are CT scans after various radio frequency ablation (RFA) tests.
Figure 55:
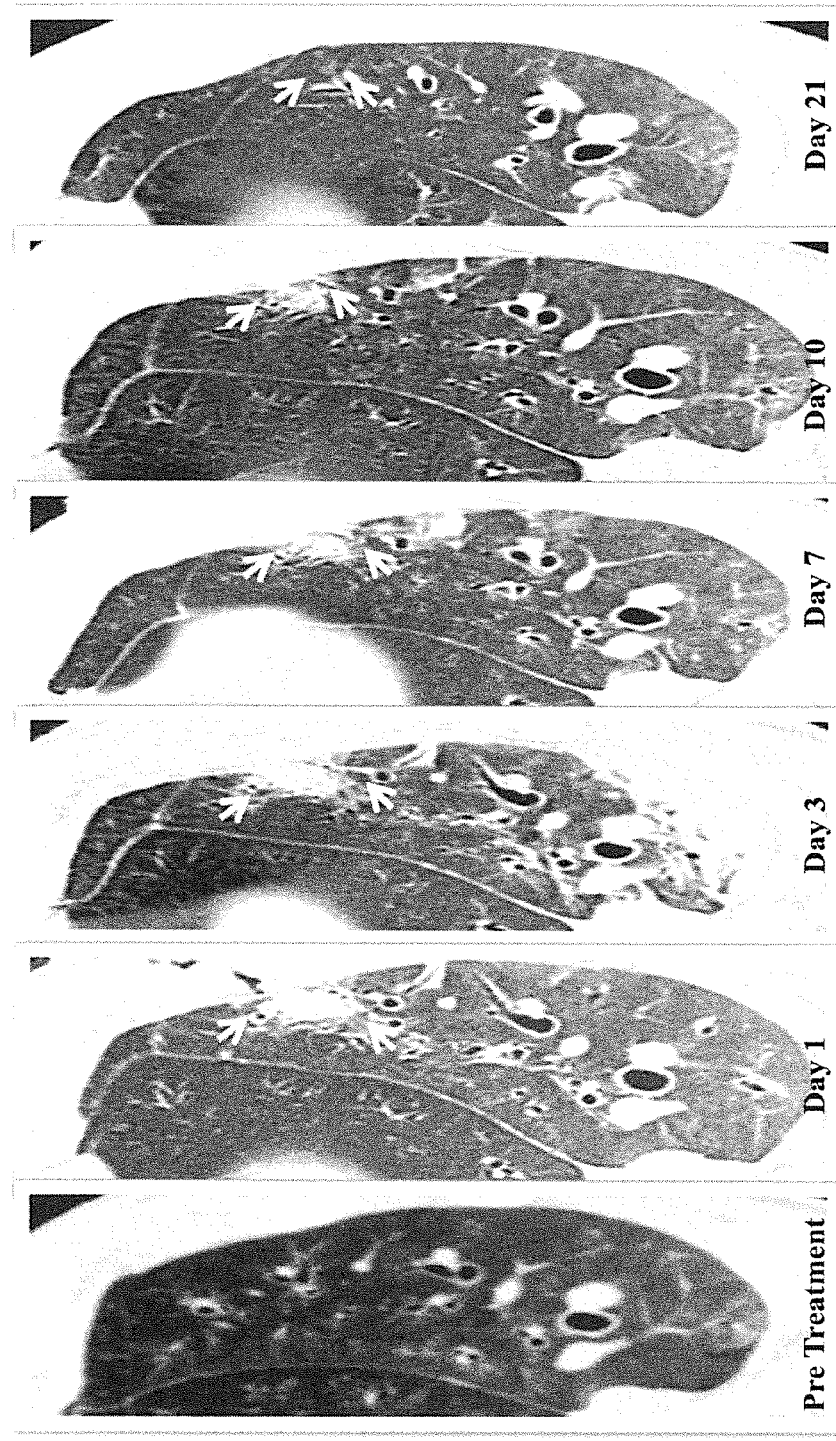
FIG. 55 are CT scans after electroporation in combination with low dose cisplatin (ECT)
Figure 56:
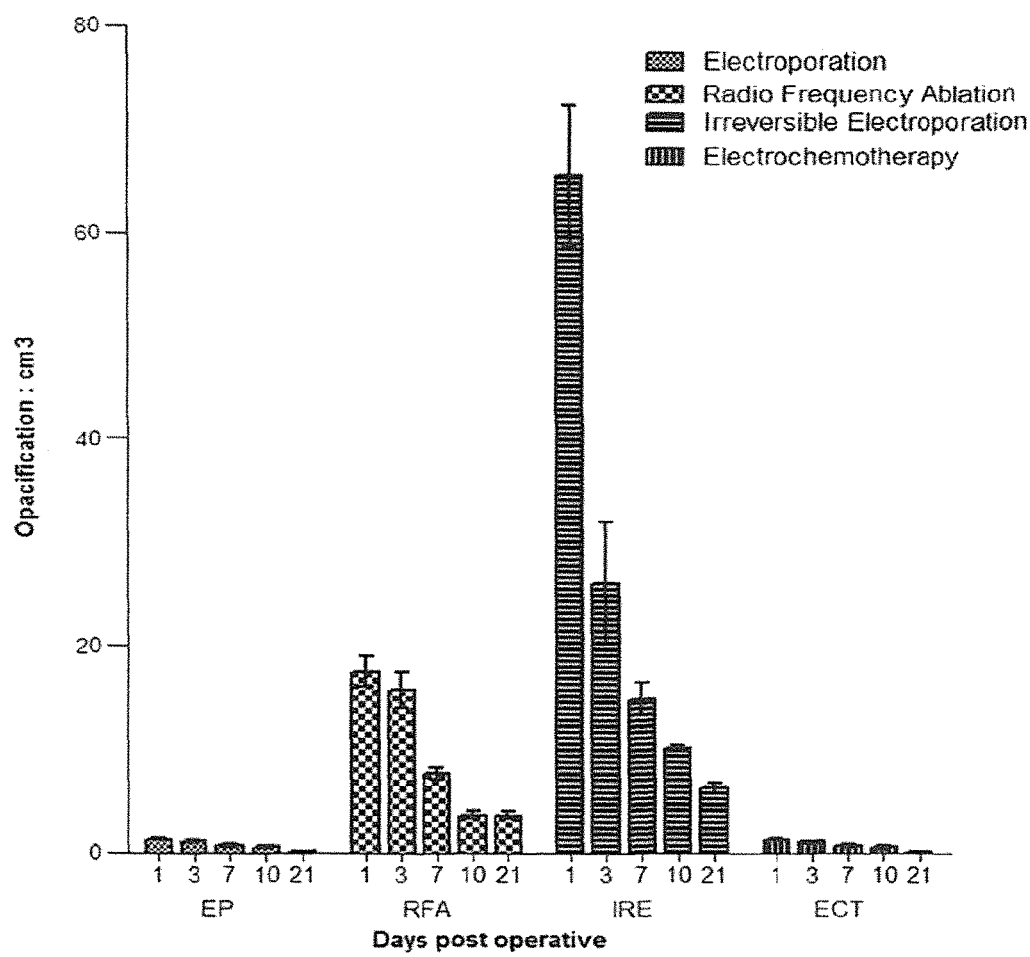
FIG. 56 is a bar chart of opacification from CT data associates with swelling/bleeding and trauma.
Figure 57:
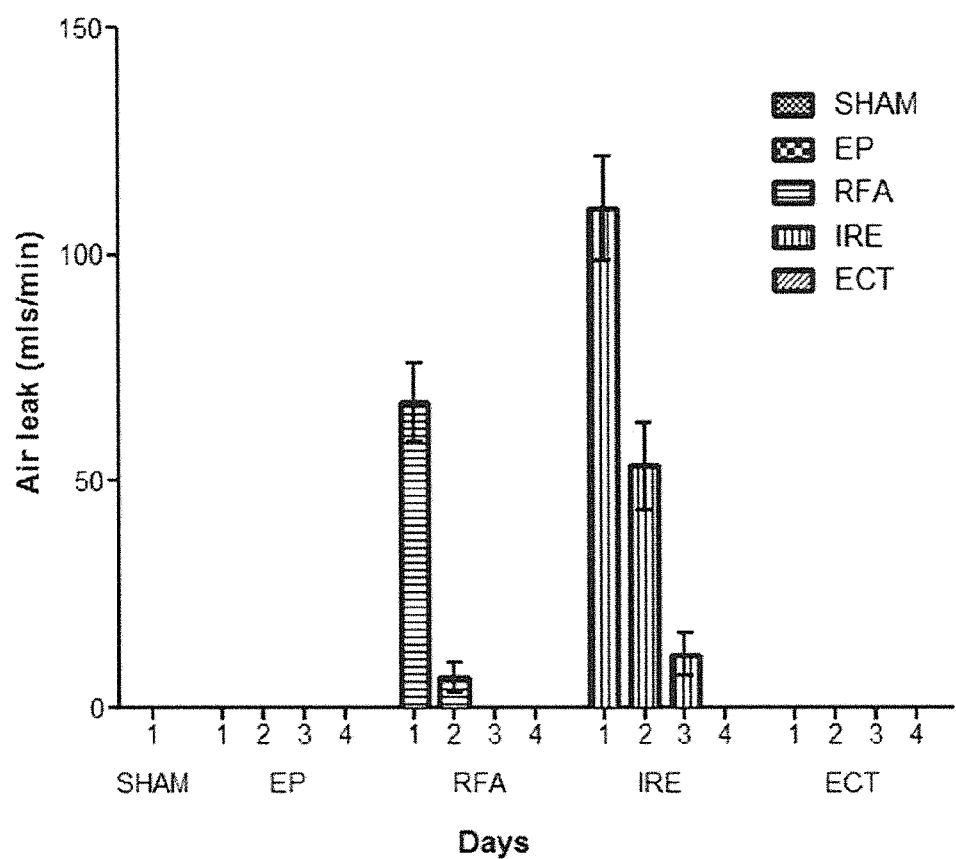
FIG. 57 is a bar chart of airleak.
Figure 58:
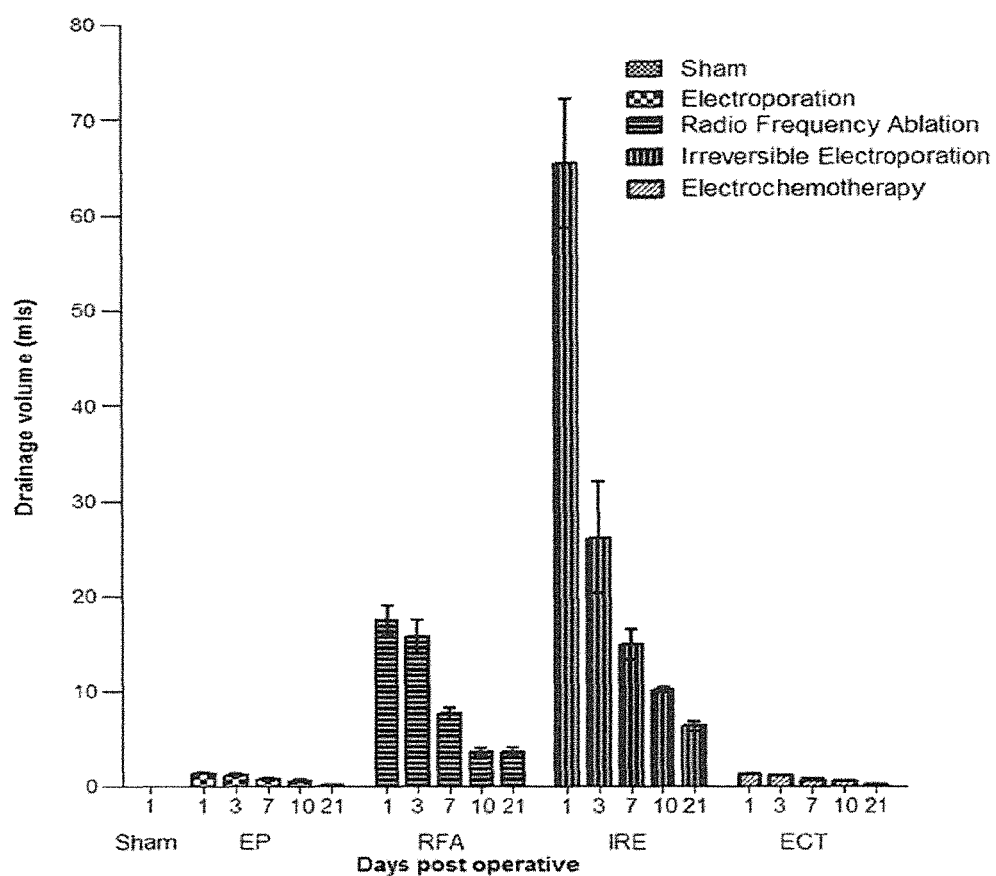
FIG. 58 is a bar chart of drainage/bleeding.

B. Evaluation of the device on porcine lung tissue has demonstrated in comparison to radio frequency ablation with the LeVeen needle that the device of the invention results in a significant reduction in trauma as measured by analysing air leaks (FIG. 57) and quantifying the drainage from bleeding (FIG. 58) in the hours and days post procedure. We also utilised CT scans of lung tissue pre and post treatment, comparing RFA to Electroporation with the device. The CT scan data (FIG. 54/55) clearly demonstrated from the degree of opacification (FIG. 56 from CT data associated with swelling/bleeding and trauma) with the device of the invention that it delivers a more targeted treatment with a substantial reduction in collateral damage to surrounding tissues relative to RFA with the LeVeen needle. FIG. 5 shows CT scans of porcine lung tissue pre-treatment with RFA using a LeVeen needle array. Significant trauma is observed immediately afterwards in the region between the arrows indicating significant bleeding and inflammation. In contrast, FIG. 55 shows CT scans of porcine lung tissue pre-treatment with electroporation using the device of the invention. Minimal trauma is observed immediately afterwards in the region between the yellow arrows indicating a targeted treatment with minimal impact on surrounding healthy tissue.

Figure 59:
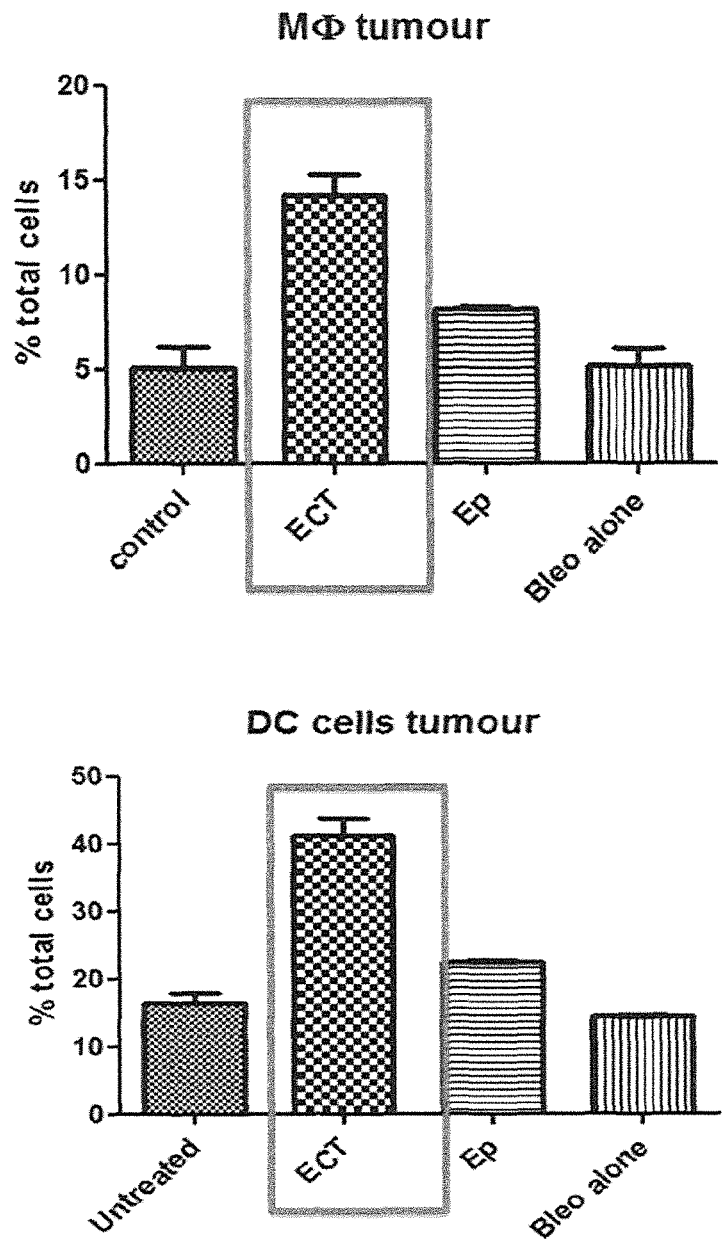
FIG. 59 are bar charts of the effect of electroporation on the immune system.
Figure 59:
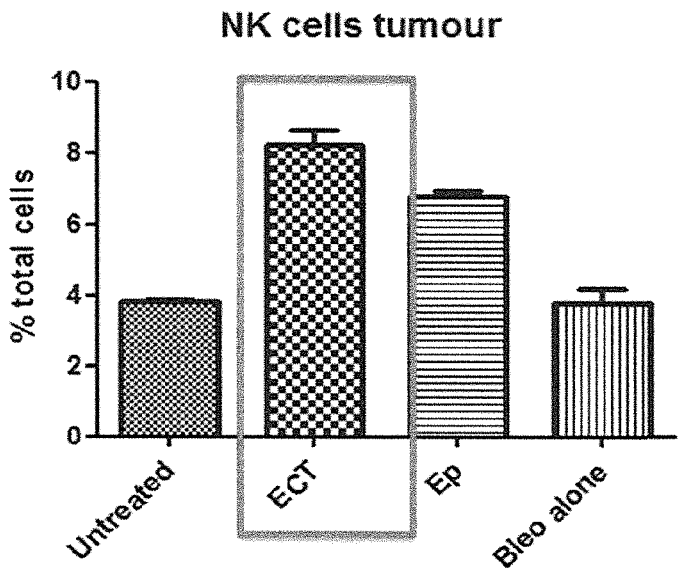
Figure 59:
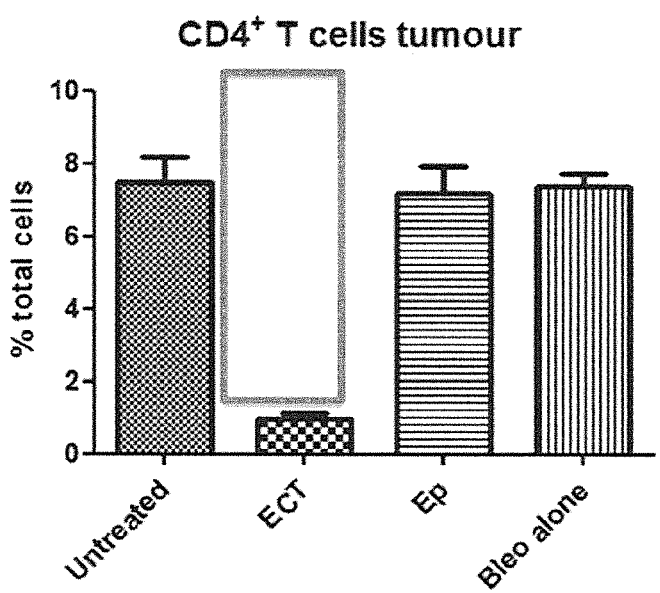
Figure 59:
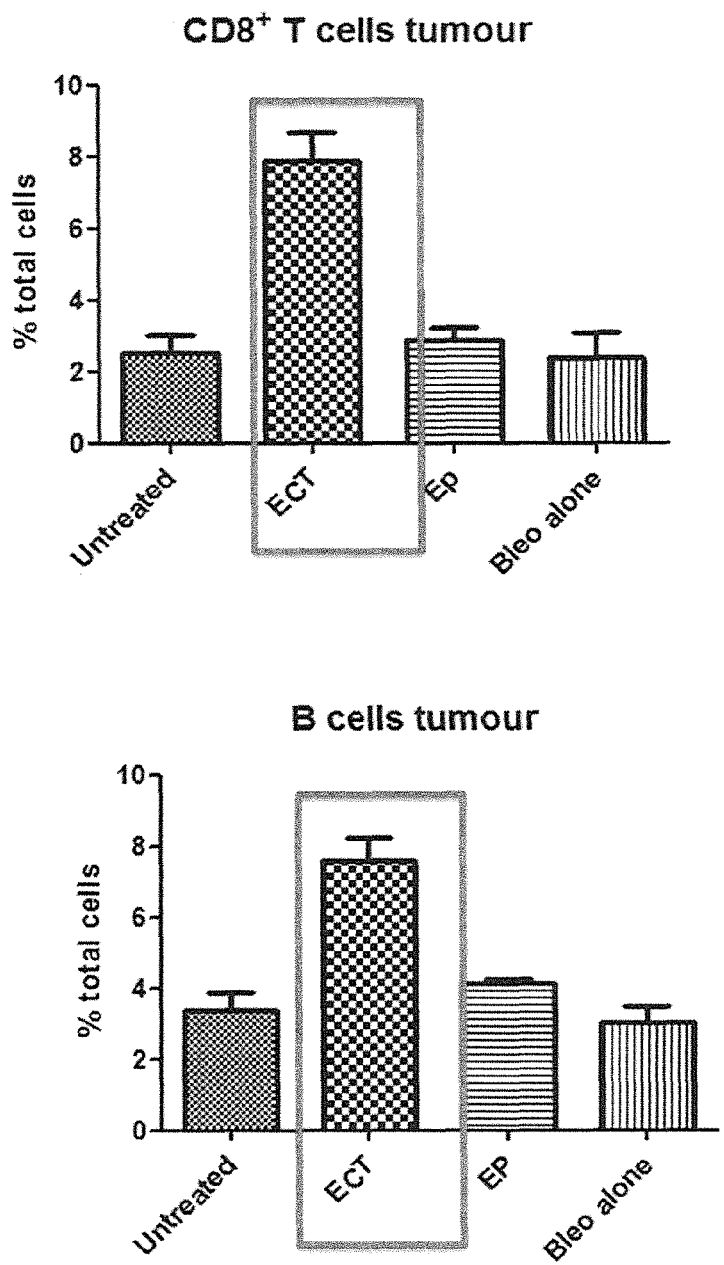

Priming—FIG. 59

There is increasing evidence to indicate that the presence within the tumour mass of tumour infiltrating lymphocytes (TILs) prior to surgery may provide the best prognostic indicator for overall survival. The potential to engage a strong immune response against the tumour using immunotherapy approaches is also gaining traction for many cancers and is currently demonstrating an increase in overall survival for late stage disease e.g. ipilimumab. Our ability to improve the curative intent of surgery may therefore be enhanced by facilitating an active immune engagement as a neo-adjuvant therapy.

The technology of electroporation offers significant potential as a neo-adjuvant therapy in that it can facilitate both perfusion and absorption of low dose chemotherapy agents while simultaneously triggering a robust immune cell engagement. Electroporation is a term used to describe the permeabilisation of the cell membrane following the application of a short and intense electric pulse. The permeabilisation can be temporary (reversible electroporation) or permanent (irreversible electroporation) as a function of the electrical field magnitude and duration, and the number of pulses. Positive outcomes have been achieved on cutaneous cancers, in terms of tumour reduction and quality of life improvement.

Massive cellular release of ATP post electroporation as the tumour cells die via a largely apoptotic mechanism and triggering of the damaged associated molecular pattern molecules (DAMPs) pathway leads to the infiltration of dendritic cells and other lymphocytic cells into the tumour mass post treatment.

We have demonstrated that ECT leads to a significant increase in the tumour of macrophages, dendritic, natural killer cells and significantly CD8+ T cells. Our data shows that combining ECT with immunomodulatory drugs that knock down the negative immunosuppressive feedback created leads to a widespread systemic immune response lead by tumour antigen specific CD8+ T cells.

The invention is not limited to the embodiments hereinbefore described which may be varied in construction and detail.

The invention claimed is:

1. A thoracoscopic electroporation device for carrying out electroporation on tissue, comprising
a suction head and a plurality of needle electrodes which are adapted for carrying out electroporation on tissue, the plurality of needle electrodes including a first needle electrode located generally along a central longitudinal axis of the suction head, and a plurality of second needle electrodes spaced-apart around a periphery of the suction head, the suction head having a retracted delivery configuration and an expanded deployed configuration and a balloon which is expandable from a retracted delivery configuration to an expanded deployed configuration to bias the suction head into the expanded deployed configuration, wherein the balloon includes at least two balloon elements which are axially spaced-apart with respect to a longitudinal axis of the device, wherein at least some of the second needle electrodes extend parallel to the central longitudinal axis in the radially retracted delivery configuration and in the radially expanded deployed configuration, and wherein the at least some of the second needle electrodes are movable on expansion of the balloon from a radially retracted configuration to a deployed radially expanded configuration.

2. The device as claimed in claim 1, wherein the suction head is cup-shaped.

3. The device as claimed in claim 1, wherein the suction head includes an inner part and an outer part which extends radially outwardly of the inner part in the deployed configuration.

4. The device as claimed in claim 3, wherein the outer part is flexible with respect to the inner part.

5. The device as claimed in claim 3, wherein the inner part is of a rigid material and the outer part is of a flexible material.

6. The device as claimed in claim 3, wherein the outer part is movable from a retracted delivery configuration to an extended deployed configuration.

7. The device as claimed in claim 1, wherein the suction head includes passages for at least some of the needles, the needles being movable though the passageways from the retracted configuration to the deployed configuration.

8. The device as claimed in 1, wherein at least some of the electrodes are movable axially from a retracted configuration to a deployed configuration, the needles extending from the suction head in the deployed configuration.

9. The device as claimed in claim 1, wherein the device includes a shaft which extends from the suction head.

10. The device as claimed in claim 1, further comprising a vacuum applier for gripping the suction head to tissue.

11. The device as claimed in claim 1, wherein the first needle electrode is a hollow needle.

12. The device as claimed in claim 1, wherein the first needle electrode extends through a central channel in the suction head.

13. A method for carrying out electroporation on tissue comprising:

providing a suction head and a plurality of needle electrodes, the plurality of needle electrodes including a first needle electrode located generally along a central longitudinal axis of the suction head, and a plurality of second needle electrodes spaced-apart around a periphery of the suction head, the suction head having a retracted delivery configuration and an expanded deployed configuration and a balloon which is expandable from a retracted delivery configuration to an expanded deployed configuration to bias the suction head into the expanded deployed configuration, wherein the balloon includes at least two balloon elements which are axially spaced-apart with respect to a longitudinal axis of the device, wherein at least some of the second needle electrodes extend parallel to the central longitudinal axis in the radially retracted delivery configuration and in the radially expanded deployed configuration and wherein the at least some of the second electrodes are movable on expansion of the balloon from a radially retracted configuration to a deployed radially expanded configuration;

delivering the suction head to tissue in the retracted configuration;

deploying the suction head at a site of interest;

applying a vacuum to the suction head;

advancing the needles from the deployed suction head; and using the needle electrodes, applying electroporation to tissue at the site of interest.

14. The method as claimed in claim 13, further comprising the step of delivering a therapeutic agent to the tissue at the site of interest before, during, or after applying electroporation.

15. The method as claimed in claim 13, wherein the site of interest is in a region of a lung.

* * * * *